(12) United States Patent
Wayman et al.

(10) Patent No.: US 9,750,529 B2
(45) Date of Patent: Sep. 5, 2017

(54) SAFETY STYLET

(75) Inventors: Annica Wayman, Morris Plains, NJ (US); Michael Meehan, Glen Rock, NJ (US); Christina D'Arrigo, Hoboken, NJ (US); Douglas Tyukody, Waldwick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1373 days.

(21) Appl. No.: 12/313,661

(22) Filed: Nov. 21, 2008

(65) Prior Publication Data

US 2009/0299400 A1 Dec. 3, 2009

Related U.S. Application Data

(60) Provisional application No. 60/989,559, filed on Nov. 21, 2007.

(51) Int. Cl.
*A61B 17/34* (2006.01)
*A61B 17/06* (2006.01)
*A61B 17/32* (2006.01)
*A61B 90/00* (2016.01)

(52) U.S. Cl.
CPC ...... *A61B 17/3401* (2013.01); *A61B 17/3472* (2013.01); *A61B 2017/06085* (2013.01); *A61B 2017/320044* (2013.01); *A61B 2090/0801* (2016.02)

(58) Field of Classification Search
CPC .......................... A61B 17/3401; A61B 17/3472
USPC ............ 604/164.01, 164.04, 164.06, 164.07, 604/164.11, 158; 606/185, 167, 184
See application file for complete search history.

(56) References Cited

U.S. PATENT DOCUMENTS

| | | | |
|---|---|---|---|
| 4,405,307 A | * | 9/1983 | Taylor ...................... 604/165.01 |
| 4,636,200 A | | 1/1987 | Vaillancourt |
| 4,721,506 A | | 1/1988 | Teves |
| 5,100,387 A | | 3/1992 | Ng |

(Continued)

FOREIGN PATENT DOCUMENTS

| | | |
|---|---|---|
| EP | 0548612 A1 | 6/1993 |
| EP | 0650699 A1 | 5/1995 |

(Continued)

OTHER PUBLICATIONS

U.S. Appl. No. 12/275,570.

(Continued)

*Primary Examiner* — Sarah W Aleman
(74) *Attorney, Agent, or Firm* — The Webb Law Firm

(57) ABSTRACT

A stylet for insertion within a cannula interior of a needle is disclosed. The stylet includes a solid elongated shaft having a proximal end adapted for engagement with a needle hub, and a distal end having a surface modified profile. The surface modified profile increases the penetration force required to penetrate human skin. The ratio of the penetration force of a stylet having an unmodified distal end to the stylet having a surface modified profile is at least 1:1.4, or greater. The surface modified profile may be a roughened surface, a buffed surface and/or a blunted surface. The surface modified profile may include a yieldable material disposed over at least a portion of the distal end. A needle assembly having a stylet having a surface modified profile is also disclosed.

15 Claims, 25 Drawing Sheets

(56) References Cited

U.S. PATENT DOCUMENTS

| | | | |
|---|---|---|---|
| 5,257,980 A * | 11/1993 | Van Antwerp et al. | 604/506 |
| 5,868,684 A * | 2/1999 | Åkerfeldt et al. | 600/564 |
| 6,059,801 A | 5/2000 | Samimi | |
| 6,837,896 B2 * | 1/2005 | Matsutani et al. | 606/167 |
| 7,963,956 B2 * | 6/2011 | Kunst | 604/890.1 |
| 2002/0169471 A1 | 11/2002 | Ferdinand | |
| 2005/0137605 A1 * | 6/2005 | Assell et al. | 606/96 |
| 2007/0066987 A1 | 3/2007 | Scanlan, Jr. et al. | |
| 2007/0106219 A1 * | 5/2007 | Grabinsky | 604/164.01 |

FOREIGN PATENT DOCUMENTS

| | | |
|---|---|---|
| JP | 1-146559 A | 6/1989 |
| JP | H-05123331 A | 5/1993 |
| JP | 7-250840 A | 10/1995 |
| JP | 2004-208971 A | 7/2004 |
| JP | 2006-223653 A | 8/2006 |

OTHER PUBLICATIONS

U.S. Appl. No. 12/275,604.
U.S. Appl. No. 12/275,636.
Campbell et al. "Incidence of Tissue Coring with the 25-Gauge Quincke and Whitacre Spinal Needles", Regional Anesthesia, Nov.-Dec. 1996, pp. 582-585, vol. 21 issue 6.
Ozyurt et al. "Tissue Coring with Spinal Needles", Letters to the Editor, May 9, 2000, p. 665.
Puolakka et al. "Microscopic Analysis of Three Different Spinal Needle Tips After Experimental Subarachnoid Puncture", Regional Anesthesia and Pain Medicine, Mar.-Apr. 2000, pp. 163-169, vol. 25 No. 2, American Society of Regional Anesthesia and Pain Medicine.

* cited by examiner

18G STYLET 1.00KX MAGNIFICATION, SIGNAL A=SE2, APERTURE SIZE=30.00 μm, EHT=10.00kV, WD=18.2mm, I PROBE=200.0nA

18G STYLET 1.00KX MAGNIFICATION, SIGNAL A=SE2, APERTURE SIZE=30.00 μm, EHT=10.00kV, WD=13.4mm, I PROBE=200.0nA

18G STYLET HAVING DISTAL TIP BLUNTED AND SANDBLASTED AT 455X MAGNIFICATION

18G STYLET HAVING DISTAL TIP BLUNTED AND SANDBLASTED AT 294X MAGNIFICATION

SAFETY STYLET

CROSS REFERENCE TO RELATED APPLICATION

This application claims priority to U.S. Provisional Patent Application No. 60/989,559, filed Nov. 21, 2007, entitled "Safety Stylet", the entire disclosure of which is herein incorporated by reference.

BACKGROUND OF THE INVENTION

Field of the Invention

The present invention relates to stylets for use with medical needles and, more particularly, to stylets having enhanced safety features.

Description of Related Art

During certain medical procedures, particularly spinal and epidural procedures, obtaining a spinal fluid sample or delivering a medicament requires the insertion of a needle into the spine. The puncture of the needle through the skin and into the spine may result in tissue that is cored and collected inside the needle. Tissues cores from the skin that are deposited in the subarachnoid space of the spinal cord can develop into intraspinal epidermoid tumors. In order to prevent tissue coring, a stylet formed as a solid elongated member, is placed within the cannula interior of the needle and typically extends to the end of the needle tip. Generally, the stylet is designed to match the profile of its intended needle gauge. The needle is inserted through the tissue with the stylet in place therein substantially preventing tissue from coring and entering the needle interior. After insertion of the needle is completed, the stylet can be partially or completely removed from the cannula interior of the needle. In certain procedures, the stylet is reinserted into the needle after completely removing it from the needle.

Injuries caused by the stylet, referred to as "stylet sticks", can lead to seroconversion and are of continued concern in the medical environment. Stylet sticks often occur during reinsertion of the stylet, as well as during clean-up after the procedure. Accordingly, there is a general need to reduce the likelihood of sticks caused by the stylet.

SUMMARY OF THE INVENTION

In accordance with an embodiment of the present invention, a stylet for insertion within a cannula interior of a needle includes a solid elongated shaft having a proximal end adapted for engagement with a needle hub. The stylet also includes a distal end having a surface modified profile.

The ratio of the penetration force required to penetrate human skin of a stylet having an unmodified distal end to the stylet having the surface modified profile may be at least 1:1.4. The surface modified profile may be at least one of a roughened surface, a buffed surface and a blunted surface. Optionally, the surface modified profile may be obtained through at least one of a sandblasting process, an electrochemical grinding process, a buffing process, a mechanical grinding process, and an etching process. In one configuration, at least 0.002 inch of material has been removed from the distal end to form the surface modified profile. In yet another configuration, the surface modified profile includes a beveled edge. The beveled edge may have a tip angle of from about 20° to about 30°. The solid elongated shaft may be formed of a metal or metal alloy, and the distal end may have an increased bevel angle for increasing the penetration force.

In accordance with another embodiment of the present invention, a needle assembly includes a needle cannula defining a cannula interior, a needle hub supporting at least a portion of the needle cannula, and a stylet disposable within the cannula interior. The stylet includes a solid elongated shaft having a proximal end adapted for engagement with the needle hub, and a distal end having a surface modified profile.

The ratio of the penetration force required to penetrate human skin of a stylet having an unmodified distal end to the stylet having the surface modified profile may be at least 1:1.4. The surface modified profile may be at least one of a roughened surface, a buffed surface and a blunted surface. In one configuration, the surface modified profile includes a beveled edge. The beveled edge may have a tip angle of from about 20° to about 30°. In a further configuration, the needle cannula has a distal bevel having a first tip angle, and the beveled edge of the stylet has a second tip angle that is greater than the first tip angle of the needle cannula. The needle cannula may have a needle gauge of from 18 G to 29 G.

In accordance with yet another embodiment of the present invention, a stylet for insertion within a cannula interior of a needle includes a solid elongated shaft having a distal end. The stylet also includes a yieldable outer covering disposed at least partially over the distal end of the elongated shaft.

The outer covering may substantially yield upon engagement with contact with human skin. The elongated shaft may be made of a metal or metal alloy, and the yieldable outer covering may be made of a polymeric material. Optionally, the yieldable outer covering may be made of nylon, polytetrafluoroethylene, perfluoroalkoxy polymer rein, and/or fluorinated ethylene-propylene. The outer covering may have a thickness of at least 0.003 inches for stylets having an outer covering formed by coating processes. The outer covering may have a thickness of at least 0.003 inch for stylets having an outer covering formed by co-extrusion processes. The outer covering may also include a beveled edge. In a further configuration, the elongated shaft and the outer covering are co-extruded. The outer covering may further include a tip portion having a length extending over the distal end of the elongated shaft from about ¼ inch to about ½ inch. The tip portion may optionally include a beveled edge.

In yet another configuration of the present invention, a needle assembly includes a needle cannula defining a cannula interior, and a needle hub supporting at least a portion of the needle cannula. The needle assembly also includes a stylet disposable within the cannula interior. The stylet includes a solid elongated shaft having a proximal end adapted for engagement with the needle hub, and a distal end. The stylet further includes a yieldable outer covering disposed at least partially over the distal end of the elongated shaft.

The yieldable outer covering substantially yields upon engagement with contact with human skin. Optionally, the elongated shaft and the yieldable outer covering are co-extruded. In a further configuration, the needle cannula has a distal bevel having a first tip angle and the distal end of the stylet has a second tip angle that is greater than the first tip angle of the needle cannula. The outer covering may also include a tip portion having a length extending over the distal end of the elongated shaft from about ¼ inch to about ½ inch. The tip portion may also include a beveled edge.

BRIEF DESCRIPTION OF THE DRAWINGS

FIG. 1A is an exploded perspective view of the needle assembly of FIG. 1 rotated 90°.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
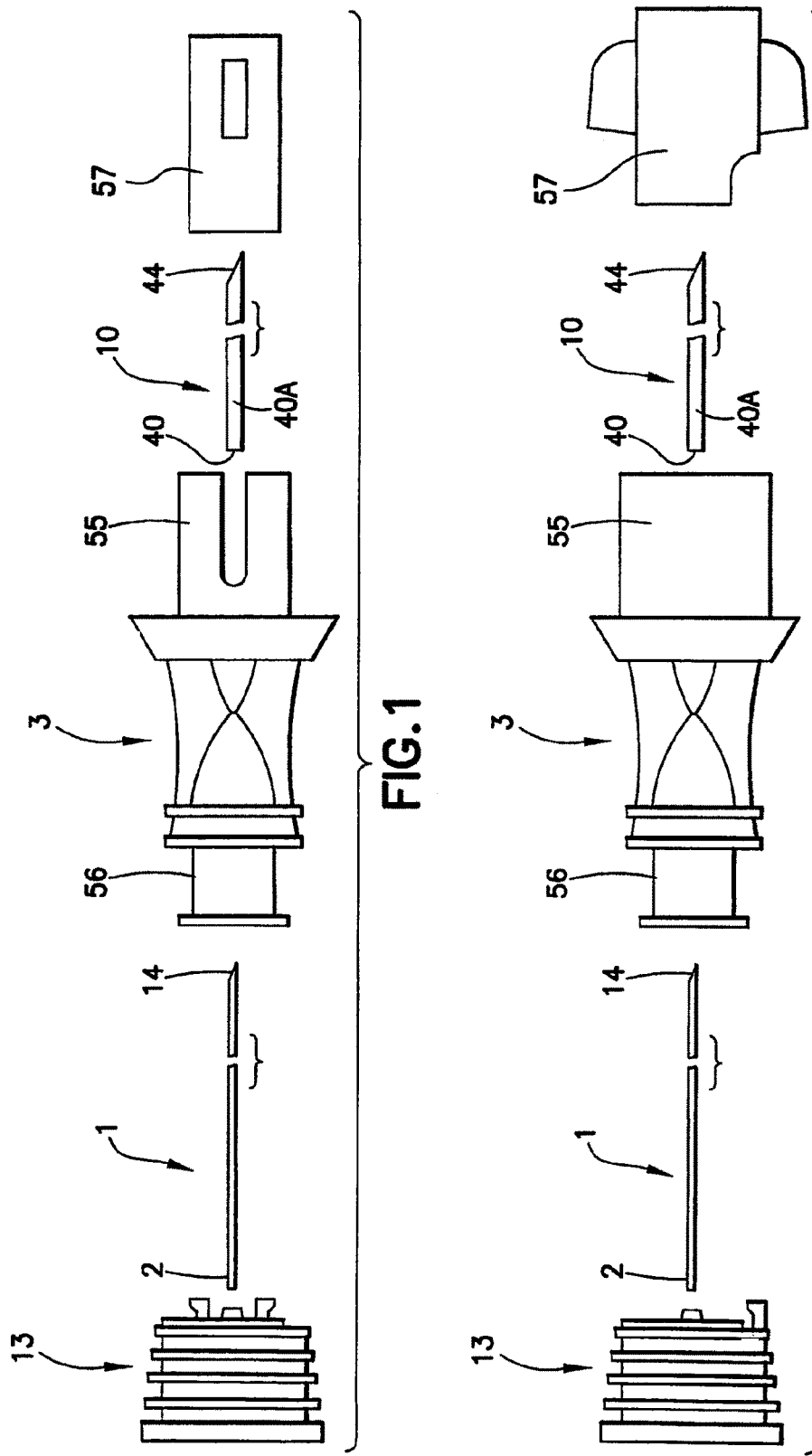
FIG. 1 is an exploded perspective view of a needle assembly in accordance with an embodiment of the present invention.
Figure 2:
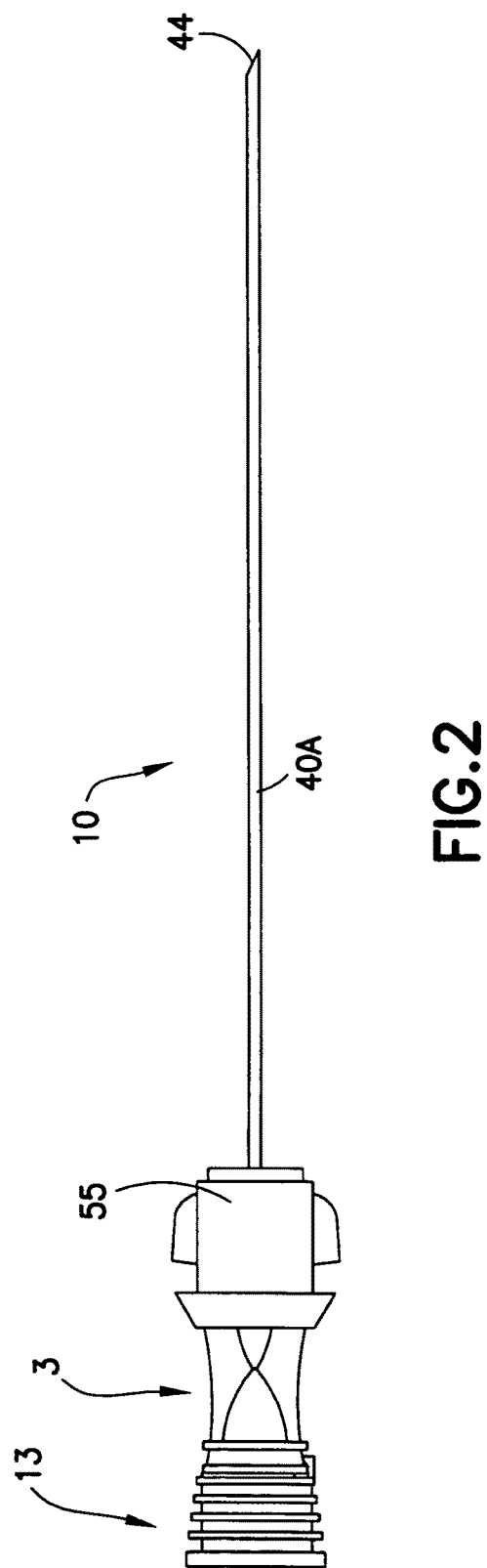
FIG. 2 is an assembled perspective view of the needle assembly of FIG. 1.

Referring to FIGS. 1-2, a stylet 1 in accordance with an embodiment of the present invention has a solid elongated shaft 5 having a distal end 14 and a proximal end 2 adapted for engagement with a needle hub 3, such as through a mating connection with a stylet handle 13. A needle 10 having a cannula interior 40 extending therethrough is also engaged with a portion of the needle hub 3, such that the needle hub 3 supports at least a portion of the needle 10. In one embodiment, the needle 10 is engaged with a distal end 55 of the needle hub 3, and the stylet 1 is disposable within the cannula interior 40 through a proximal end 56 of the needle hub 3. A needle guard 57 may optionally be provided to shield the bevel 44 provided at the distal end of the needle 10. In one configuration, the stylet 1 may have an outer diameter that is from about 0.007 inch to about 0.013 inch smaller than the inner diameter of the cannula interior 40 of the needle 10.

Figure 3:
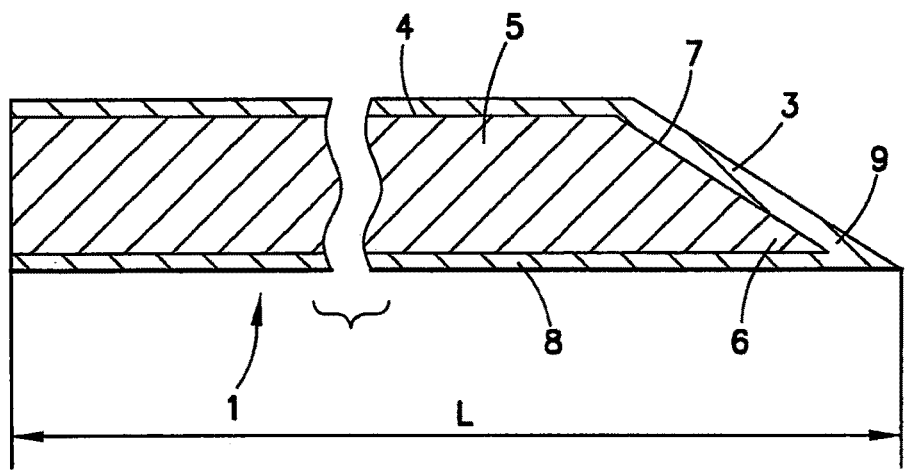
FIG. 3 is a partial cross-sectional side view of a stylet in accordance with an embodiment of the present invention.
Figure 4:
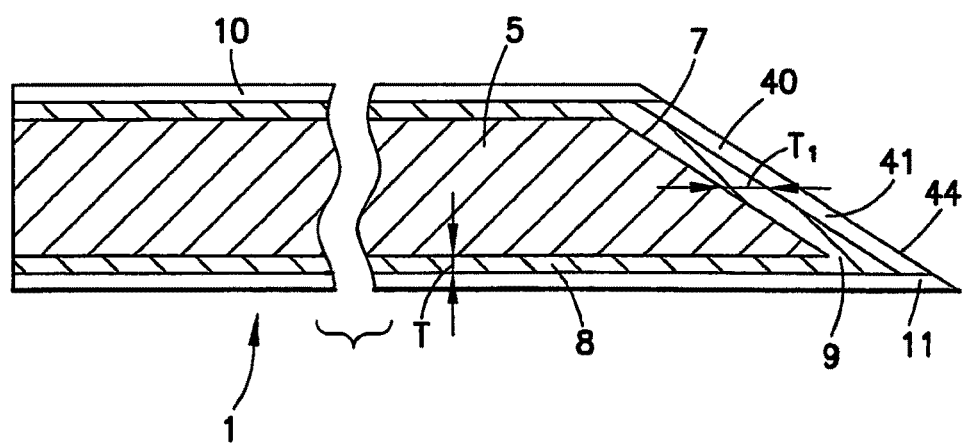
FIG. 4 is a partial cross-sectional side view of the stylet of FIG. 1 disposed within a needle cannula in accordance with an embodiment of the present invention.

Referring to FIGS. 3-4, in accordance with an embodiment of the present invention, the stylet 1 is adapted for insertion within the cannula interior 40 of a needle 10, and includes a solid elongated shaft 5, such as a tubular core, having a distal end 6, and a yieldable outer covering 8 disposed at least partially over the distal end 6 of the elongated shaft 5. As used herein, the term "yieldable" means a material capable of at least partially deflecting against a skin surface during incidental manual applied pressure. It is intended herein that the yieldable outer covering 8 will at least partially deflect during accidental or unintentional contact between the distal end 6 of the stylet 1 and a skin surface, such as a skin surface of a medical practitioner during reinsertion of the stylet 1 within the cannula interior 40 of the needle 10 or during clean-up procedures after the stylet 1 has been removed from the needle 10. It is also intended herein that an intentional penetration force in excess of a typically applied manual pressure must be applied to the stylet 1 of the present invention in order for the distal end 6 to penetrate a skin surface. In another embodiment, the stylet 1 of the present invention may be dimensioned for receipt within the cannula interior 40 of a long needle 10, such as those adapted for use in spinal and/or epidural procedures, having a needle gauge of from 18 G to 29 G. In a further embodiment, the stylet 1 of the present invention requires an intentional applied penetration force, such as along the longitudinal axis L of the elongated shaft 5, that is greater than the penetration force required for insertion of the needle 10 within a patient.

The yieldable outer covering 8 may be disposed over the distal end 6 of the elongated shaft 5 and about at least a portion of the sidewall 4 of the elongated shaft 5. The outer covering 8 may have an outer tip 9 with at least a portion of the outer tip 9 extending over the distal end 6 of the elongated shaft 5. As shown in FIG. 3, the outer tip 9 of the outer covering 8 may substantially correspond to the profile of the distal end 6. In a further embodiment, the elongated shaft 5 may include a beveled edge 7, and the yieldable outer covering 8 may also include a beveled edge 41 which substantially corresponds to the beveled edge 7 of the elongated shaft 5. Optionally, the elongated shaft 5 may include a blunted profile and the yieldable outer covering 3 may include a beveled edge 3. The beveled edge 41 of the yieldable outer covering 8 may also substantially correspond to a bevel 44 provided at the distal end 11 of the needle 10, which limits the amount of space between the distal end 11 and the yieldable outer covering 8. During a medical procedure, the stylet 1 may limit the needle 10 from coring tissue by substantially blocking the coring surfaces on the tip of the needle and the cannula interior 40, such as the interior flow path of the needle 10.

The yieldable outer covering 8 may be provided by any suitable process, such as a co-extrusion process or by coating a portion or the entire elongated shaft 5 with the yieldable material. In a further configuration, the elongated shaft 5 may be made from a polymeric material, metal or metal alloy, and the outer covering 8 may be made of a polymeric material. Example yieldable outer covering materials include nylon, polytetrafluoroethylene, perfluoroalkoxy polymer resin, and/or fluorinated ethylene-propylene. The yieldable outer covering 8 may be provided on the elongated shaft at any suitable maximum thickness T such that the stylet 1 may be received with the cannula interior 40 of the needle 10, shown in FIG. 4. In a further embodiment, the yieldable outer covering 8 is provided on the elongated shaft 5 at a minimum thickness T of at least 0.0003 inch. Optionally, the yieldable outer covering 8 may be provided adjacent the beveled edge 41 at an increased thickness $T_1$, as compared to the thickness T of the remainder of the elongated shaft 5. Referring again to FIG. 4, in one embodiment, the beveled edge 7 of the elongated shaft 5 may be provided such that the bevel 7 is substantially co-planar with the bevel 44 of the distal end 11 of the needle 10. In another embodiment, the beveled edge 7 of the elongated shaft 5 may be recessed slightly into the cannula interior 40 with respect to the bevel 44 of the distal end 11 of the needle 10.

Figure 5:
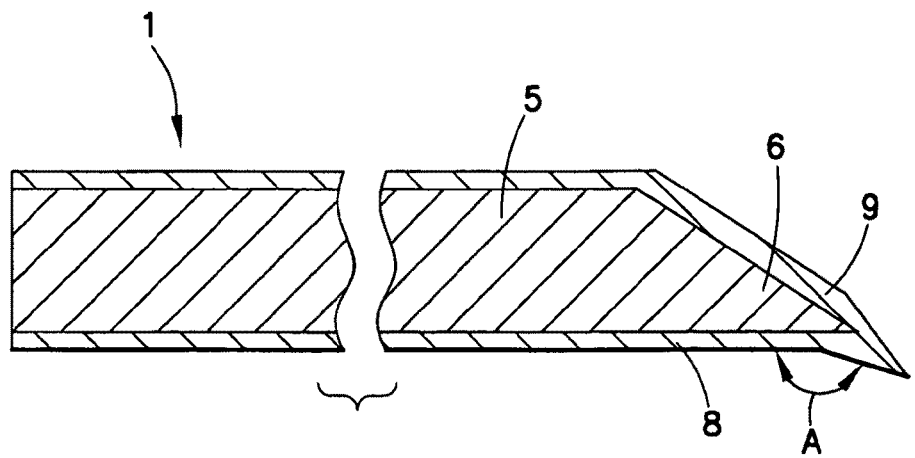
FIG. 5 is a partial cross-sectional side view of the stylet of FIG. 1 having a deflectable tip.
Figure 6:
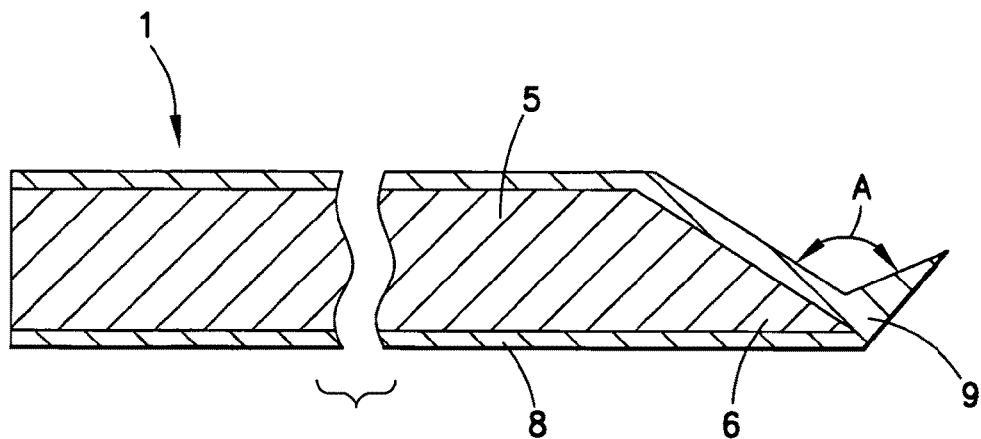
FIG. 6 is a partial cross-sectional side view of the stylet of FIG. 1 having a deflectable tip.
Figure 7:
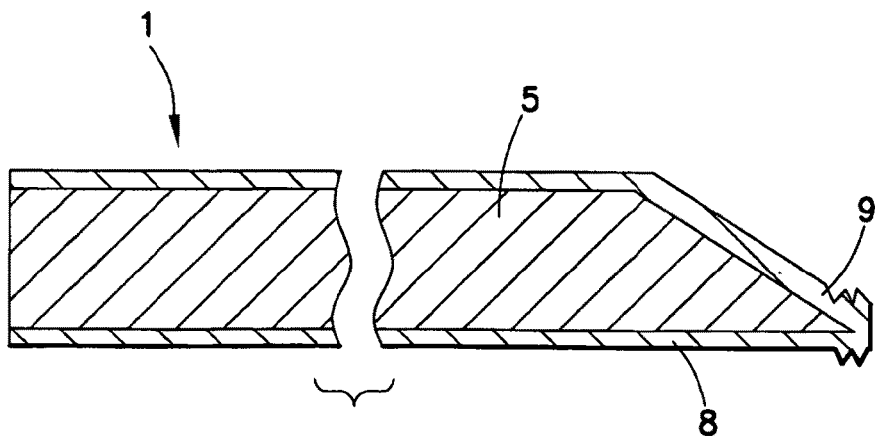
FIG. 7 is a partial cross-sectional side view of the stylet of FIG. 1 having a deflectable tip.

In one embodiment, the yieldable outer covering substantially yields upon contact with human skin. As shown in FIGS. 5-6, the yieldable outer covering 8, such as the outer tip 9, may be deflectable with respect to the elongated shaft 5 a deflection angle A from the longitudinal axis L, shown in FIG. 3. In one embodiment, the deflection angle A may be from about 5° to about 90° upon contact with a skin surface. In yet another embodiment, the outer tip 9 may deflect in a direction that is substantially aligned with the orientation of the bevel 7 of the elongated shaft, as shown in FIG. 5. In another embodiment, the outer tip 9 may deflect in a direction that is substantially opposite the orientation of the bevel 7 of the elongated shaft, as shown in FIG. 6. In accordance with an alternate embodiment, the yieldable covering 8, such as the outer tip 9, is capable of being crumpled upon contact with a skin surface, in a direction that compacts the yieldable covering 8 toward the elongated shaft 5 as shown in FIG. 7.

Figure 8:
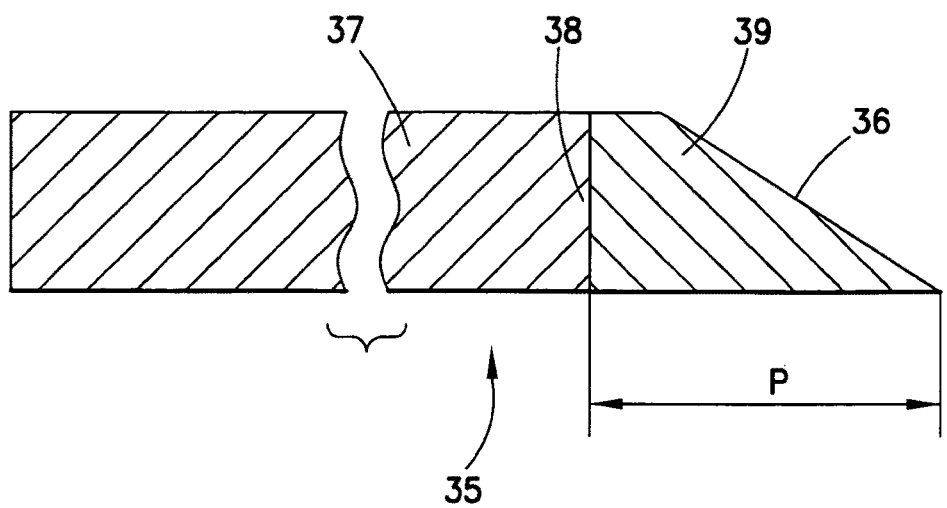
FIG. 8 is a partial cross-sectional side view of a stylet in accordance with another embodiment of the present invention.

Referring to FIG. 8, in a further embodiment of the present invention, a stylet 35 is provided having an elongated shaft 37 with a distal tip portion 39. In one embodiment, the tip portion 39 is made entirely of a yieldable outer covering material. In one configuration, the yieldable outer covering material forms a tip portion 39 having a length P extending from the distal end 38 of the elongated shaft 37 from about ¼ inch to about ½ inch. In another configuration, the tip portion 39 may include a beveled edge 36, as similarly discussed above. The tip portion 39 and the elongated shaft 37 may be co-formed, or separately formed and subsequently assembled.

Figure 9:
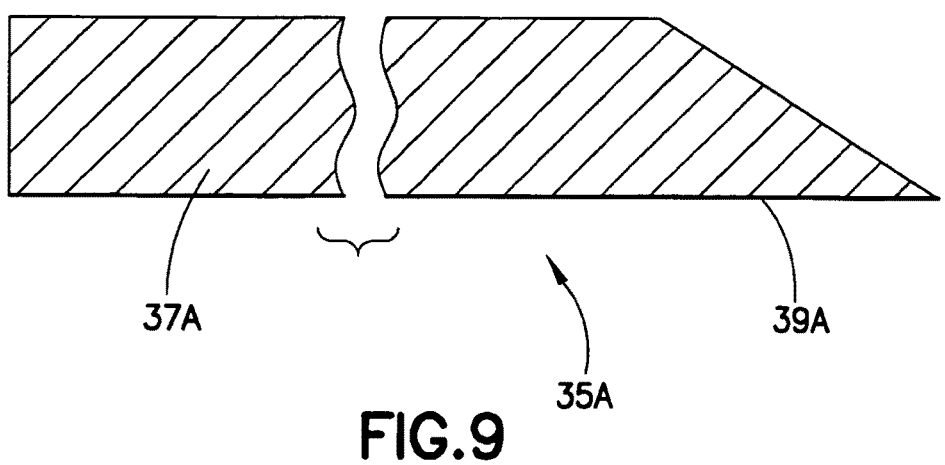
FIG. 9 is a partial cross-sectional side view of a stylet in accordance with a further embodiment of the present invention.

Referring to FIG. 9, in another embodiment of the present invention, a stylet 35A includes an elongated shaft 37A and a distal end 39A which are continuously formed from a yieldable outer covering material, such as in an extrusion process. Optionally, the distal end 39A may include a beveled edge 39A1, as similarly described above.

Figure 10:
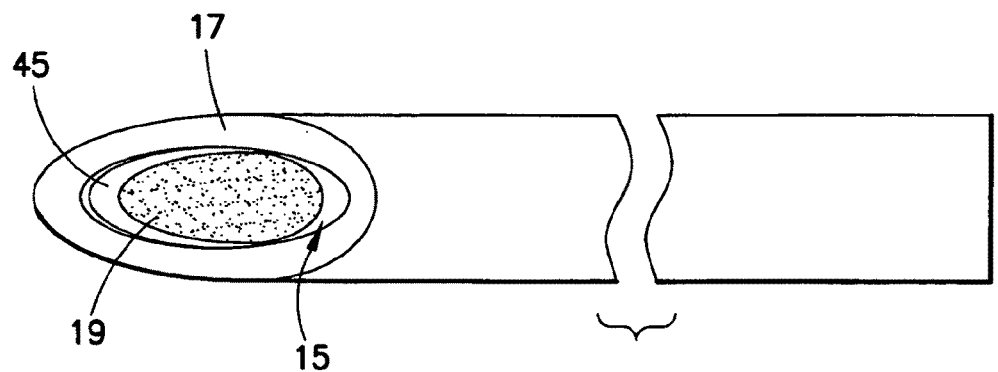
FIG. 10 is a partial top view of a stylet disposed within a needle cannula in accordance with another embodiment of the present invention.
Figure 11:
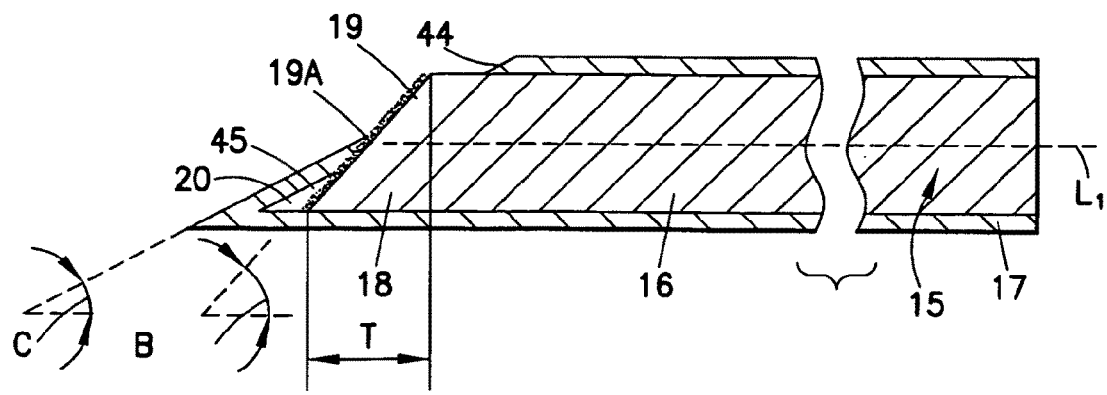
FIG. 11 is a partial cross-sectional side view of the stylet and needle cannula of FIG. 10.

Referring to FIGS. 10-11, in accordance with another embodiment of the present invention, the stylet 15 is adapted for insertion within the cannula interior 20 of a needle 17 and includes a solid elongated shaft 16, such as a tubular core, having a distal end 18 having a surface modified profile 19. As used herein, the term "surface modified" means a surface processing effect which increase the penetration force required to penetrate human skin. It is intended herein that an intentional penetration force in excess of a typically applied manual pressure must be applied to the stylet 15 of the present invention in order for the distal end 18 to penetrate a skin surface.

It is intended herein that the surface modified profile 19 will increase the penetration force required to penetrate a skin surface during accidental or unintentional contact with the distal end 6 of the stylet 15, such that the stylet 15 will not penetrate the skin surface absent intentional applied pressure to the stylet 15. As discussed above, the stylet 15 of the present invention may be dimensioned for receipt within the cannula interior 20 of a long needle 17, such as those adapted for use in anesthesia, spinal taps and/or epidural procedures, having a needle gauge of from 18 G to 29 G. In a further embodiment, the stylet 15 of the present invention requires an intentional applied penetration force, such as along the longitudinal axis $L_1$, of the elongated shaft 16, that is greater than the penetration force required for insertion of the needle 17 within a patient.

Figure 12:
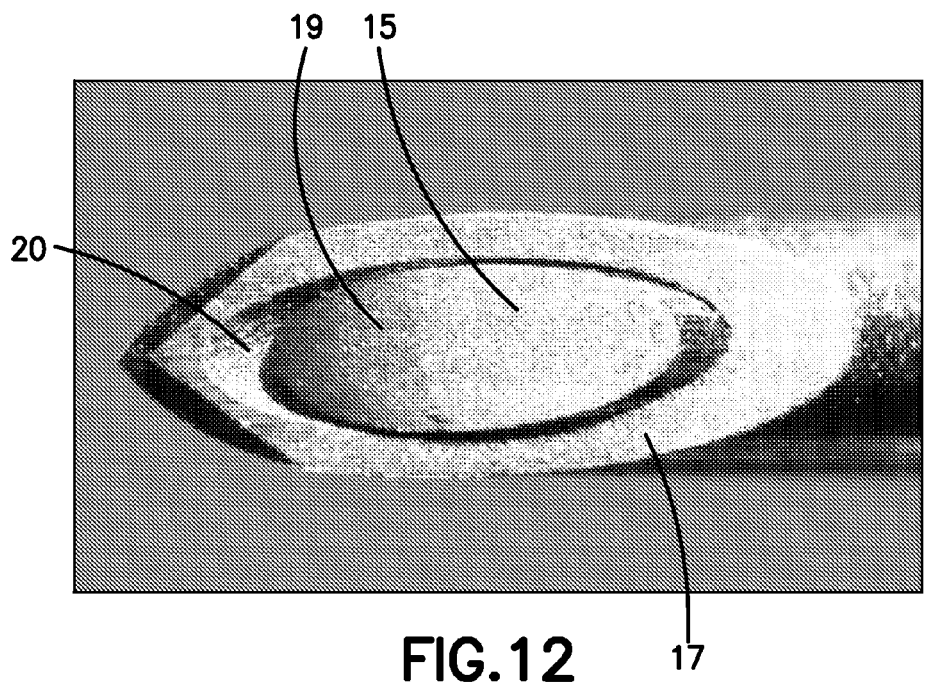
FIG. 12 is an image at 30× magnification of an 18 G stylet having a surface modified profile obtained by electrochemical grinding disposed within a needle cannula in accordance with an embodiment of the present invention.
Figure 13:
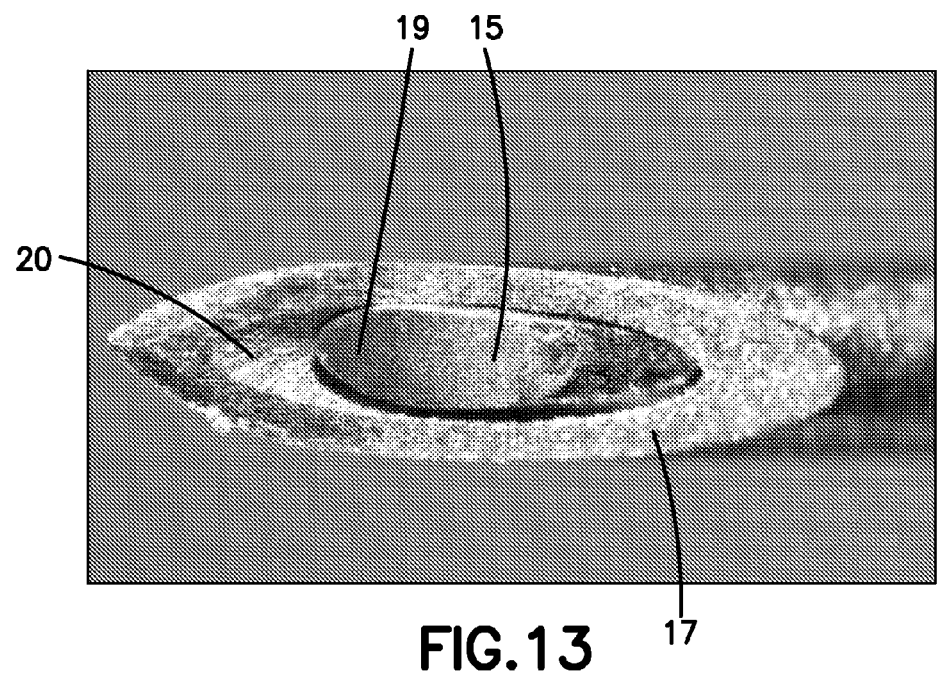
FIG. 13 is an image at 40× magnification of a 22 G stylet having a surface modified profile obtained by electrochemical grinding disposed within a needle cannula in accordance with an embodiment of the present invention.

In one embodiment, the surface modified profile is a roughened surface, a buffed surface and/or a blunted surface. In another embodiment, the surface modified profile 19 may be provided in the form of a coating layer having granular additive therein. In another embodiment, the surface modified profile 19 may be obtained through at least one of a sandblasting process, an electrochemical grinding process, a mechanical grinding process, a buffing process and an etching process. In one configuration, at least 0.002 inch of material is removed from the distal end 18 of the stylet 15 to form the surface modified profile 19. FIG. 12 shows an image at 30× magnification of an 18 G gauge stylet 15 disposed within a cannula interior 20 of a needle 17 having about 0.007 inch of material removed from the distal end 18 of the elongated shaft 16 by an electrochemical grinding process to form a surface modified profile 19. FIG. 13 shows an image at 40× magnification of a 22 G gauge stylet 15 disposed within a cannula interior 20 of a needle 17 having about 0.007 inch of material removed from the distal end 18 of the elongated shaft 16 by an electrochemical grinding process to form a surface modified profile 19.

Figure 14:
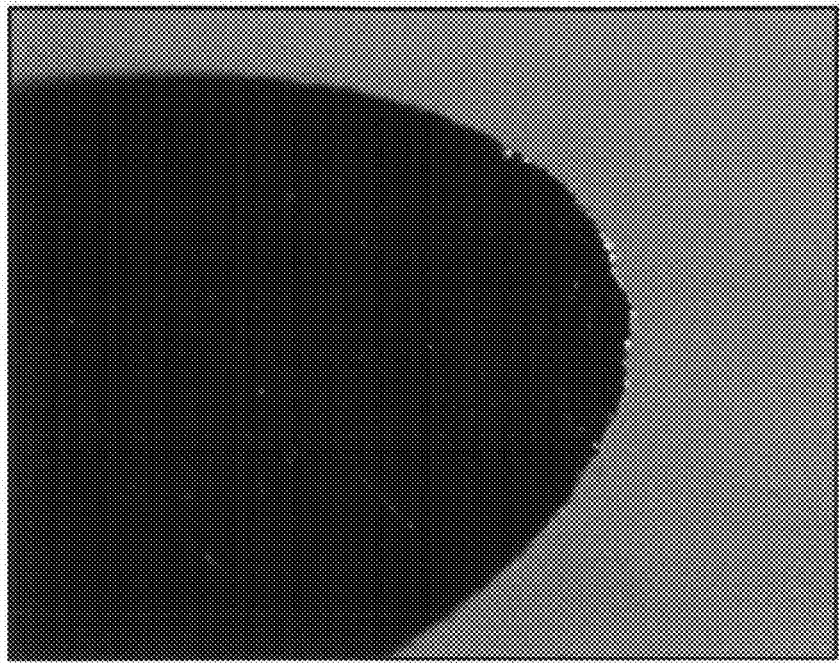
FIG. 14 is an image at 80× magnification of the distal tip of an 18 G conventional stylet.
Figure 15:
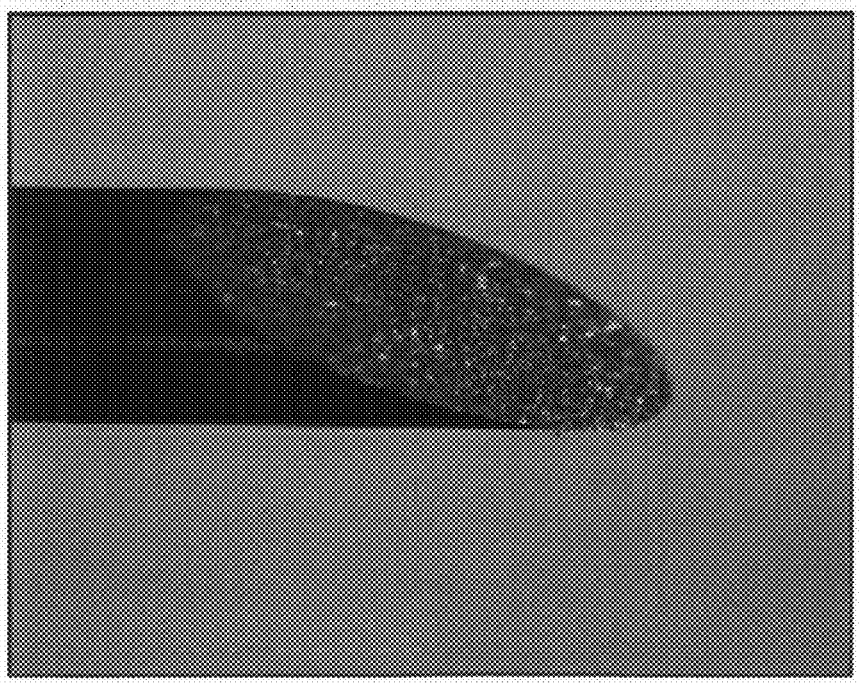
FIG. 15 is an image at 30× magnification of the beveled edge of an 18 G conventional stylet.
Figure 16:
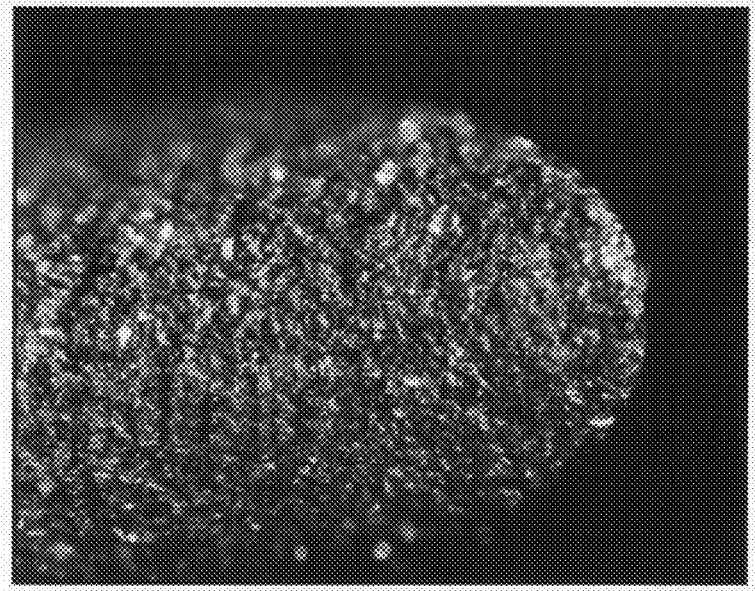
FIG. 16 is an image at 80× magnification of the distal tip of an 18 G stylet having a surface modified profile obtained by sandblasting in accordance with an embodiment of the present invention.
Figure 17:
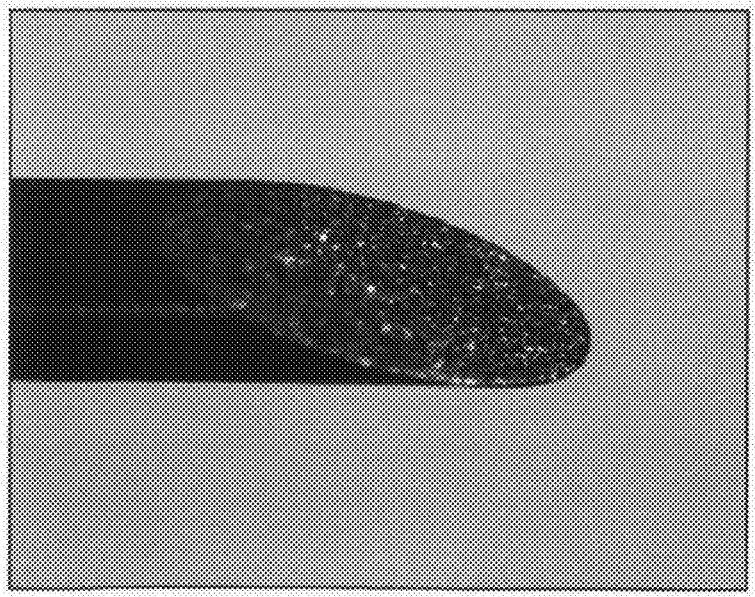
FIG. 17 is an image at 30× magnification of the beveled edge of an 18 G stylet having a surface modified profile obtained by sandblasting in accordance with an embodiment of the present invention.

Referring again to FIGS. 10-11, the surface modified profile 19 may include abraded regions of material which increase the "roughness" of the distal end 18 of the stylet 15. FIGS. 14-15 show an 18 G conventional stylet without a surface modified profile at 80× magnification. FIG. 14 shows a close-up of the distal end of the stylet and FIG. 15 shows a close-up of the entire bevel of the stylet. In both FIGS. 14-15 the surface of the stylet is relatively free of texturing. FIGS. 16-17 show an 18 G stylet having a surface modified profile obtained by sandblasting the distal end of the stylet to remove 0.004 inch of material from the stylet at 80× magnification. FIG. 16 shows a close-up of the distal end of the stylet and FIG. 17 shows a close-up of the entire bevel of the stylet. FIGS. 16-17 each show a highly textured surface of the stylet as compared to the conventional stylet shown in FIGS. 14-15.

Figure 18:
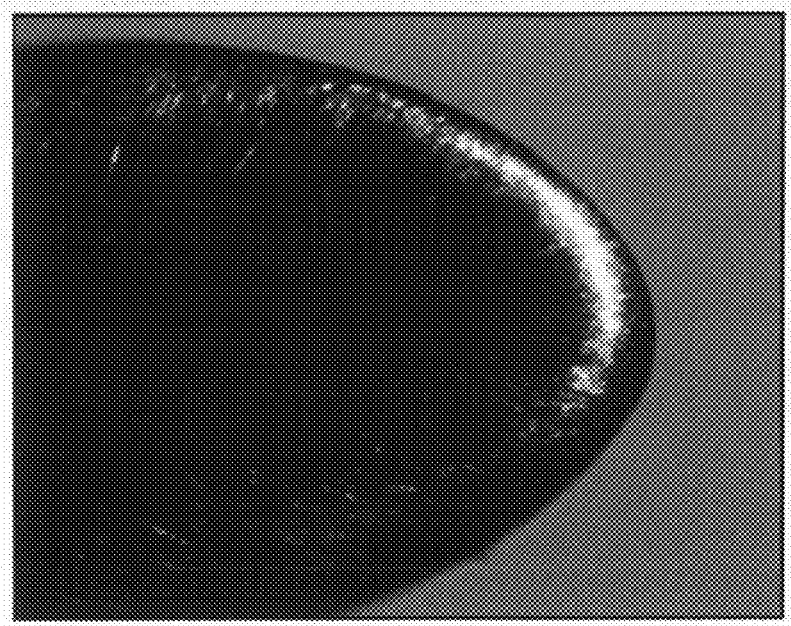
FIG. 18 is an image at 80× magnification of the distal tip of an 18 G stylet having a surface modified profile obtained by buffing in accordance with an embodiment of the present invention.
Figure 19:
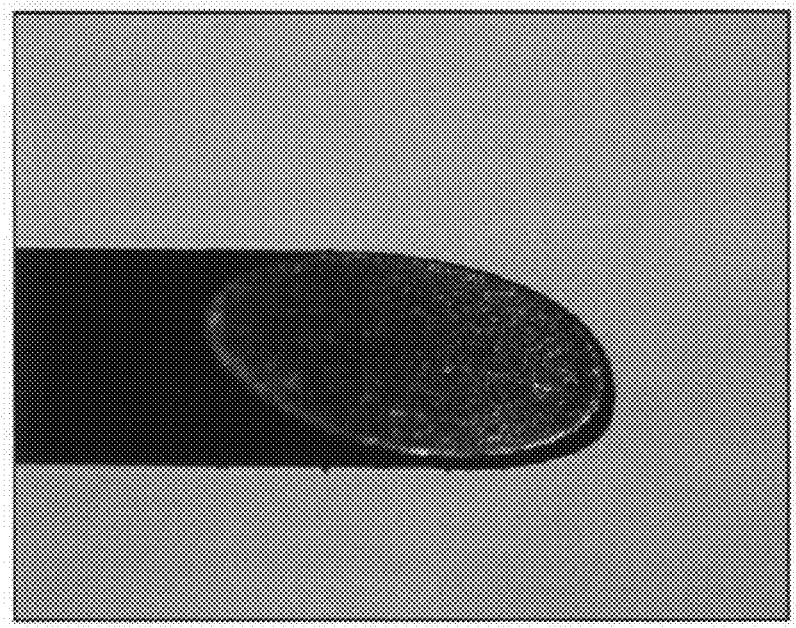
FIG. 19 is an image at 30× magnification of the beveled edge of an 18 G stylet having a surface modified profile obtained by buffing in accordance with an embodiment of the present invention.

Referring yet again to FIGS. 10-11, in another configuration the surface modified profile 19 may include buffed regions which dull the sharpness of the distal end 18 of the stylet 15. FIGS. 18-19 show an 18 G stylet having a surface modified profile obtained by buffing the distal end of the stylet to remove 0.008 inch of material from the stylet at 80× magnification.

FIG. 18 shows a close-up of the distal end of the stylet and FIG. 19 shows a close-up of the entire bevel of the stylet. FIGS. 18-19 each show a highly textured surface of the stylet as compared to the conventional stylet shown in FIGS. 14-15.

Figure 19A:
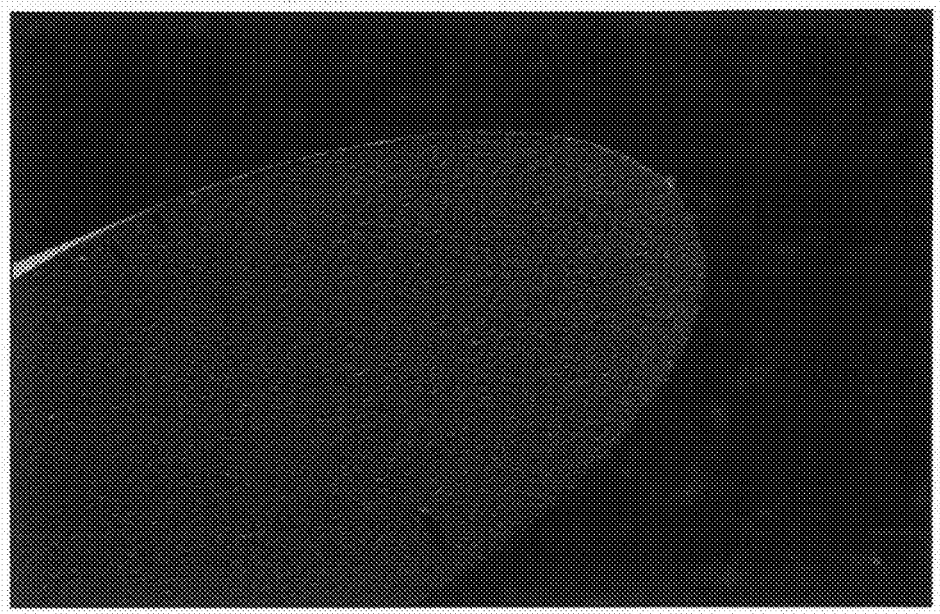
FIG. 19A is an image at 250× magnification of the distal tip of an 18 G conventional stylet.
Figure 19B:
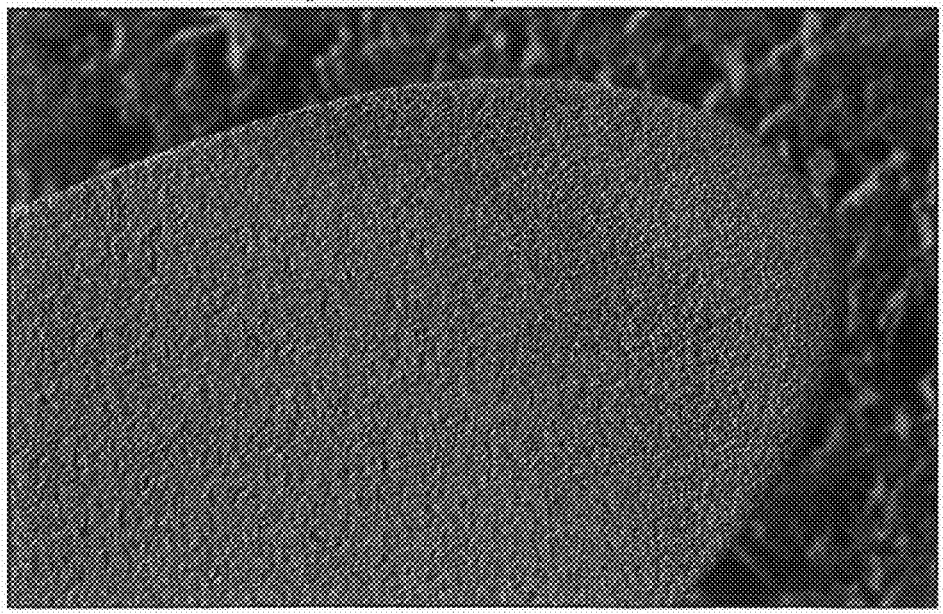
FIG. 19B is an image at 250× magnification of the distal tip of an 18 G stylet having a surface modified profile obtained by electrochemical grinding in accordance with an embodiment of the present invention.
Figure 19C:
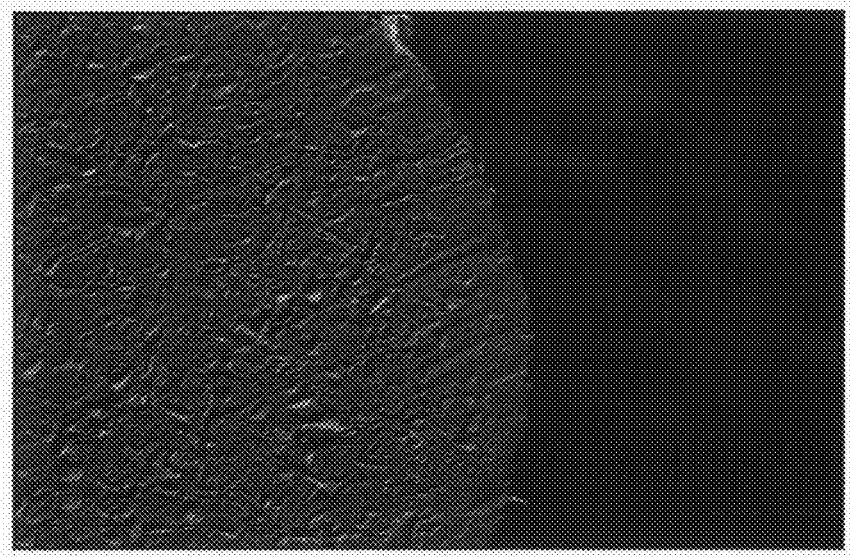
FIG. 19C is an image at 1,000× magnification of the distal tip of an 18 G conventional stylet.
Figure 19D:
FIG. 19D is an image at 1,000× magnification of the distal tip of an 18 G stylet having a surface modified profile obtained by electrochemical grinding in accordance with an embodiment of the present invention.

FIG. 19A shows the distal tip of an 18 G conventional stylet at 250× magnification. In comparison, FIG. 19B shows the distal tip of an 18 G stylet having a surface modified profile obtained by electrochemical grinding at 250× magnification. FIG. 19C shows the distal tip of an 18 G conventional stylet at 1,000× magnification. In comparison, FIG. 19D shows the distal tip of an 18 G stylet having a surface modified profile obtained by electrochemical grinding at 1,000× magnification. As shown in both FIGS. 19B and 19D, the distal tip of the 18 G stylet having a surface modified profile has increased micro-texturing as compared to the distal tip of a conventional 18 G stylet shown in FIGS. 19A and 19C.

Figure 19E:
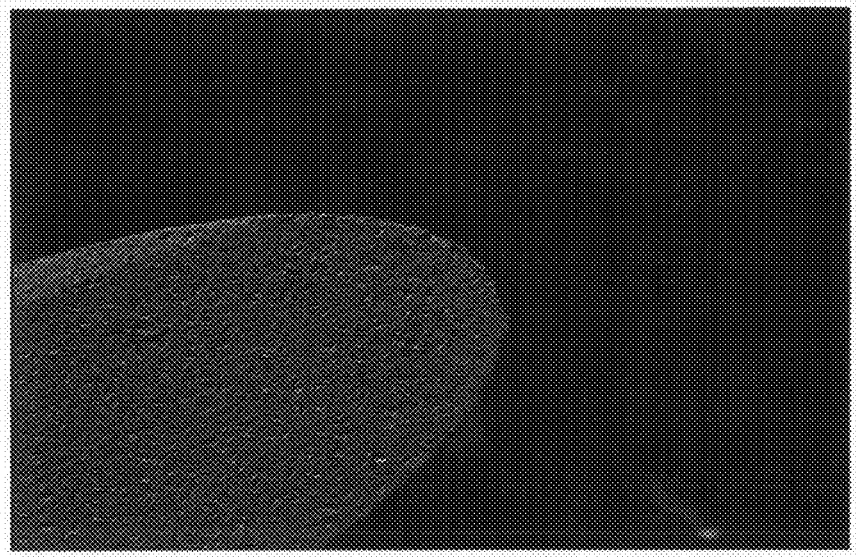
FIG. 19E is an image at 500× magnification of the distal tip of a 22 G conventional stylet.
Figure 19F:
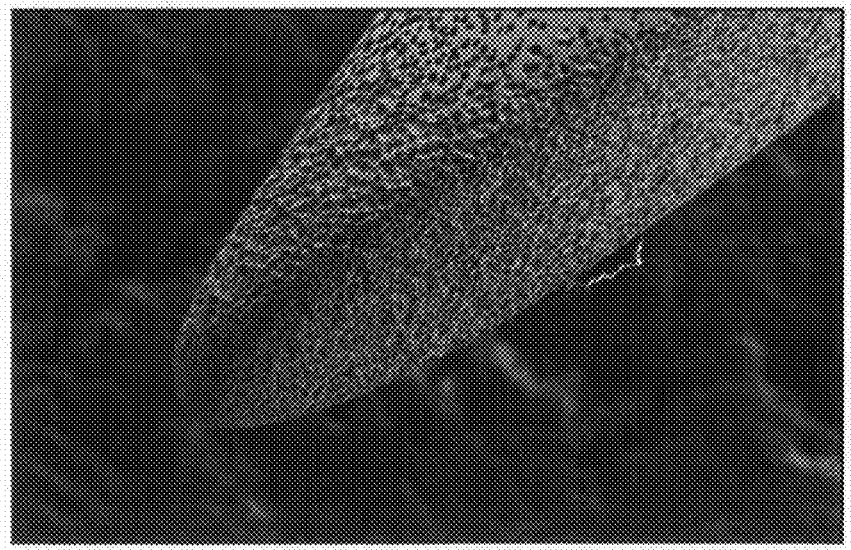
FIG. 19F is an image at 500× magnification of the distal tip of a 22 G stylet having a surface modified profile obtained by electrochemical grinding in accordance with an embodiment of the present invention.
Figure 19G:
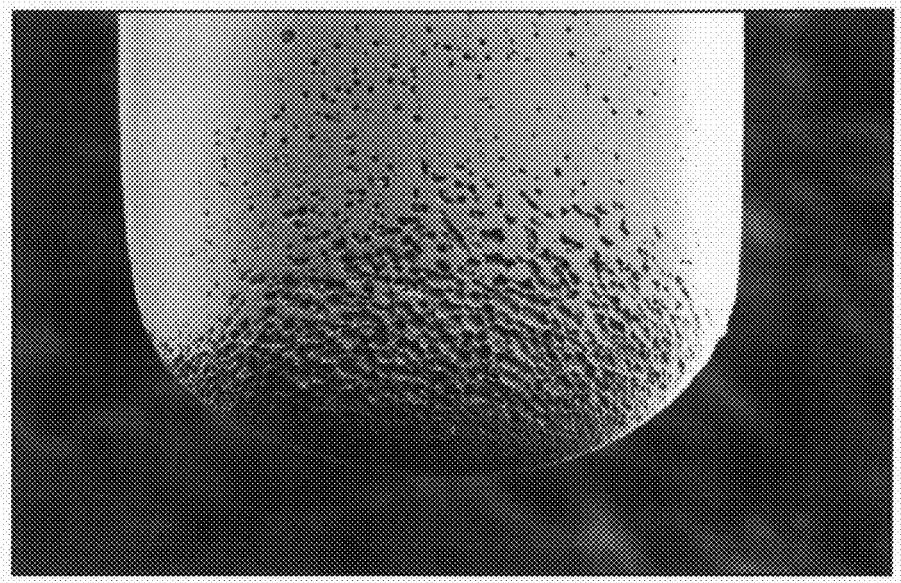
FIG. 19G is an image at 500 magnification of the distal tip of a 22 G stylet having a surface modified profile obtained by electrochemical grinding in accordance with an embodiment of the present invention.
Figure 19H:
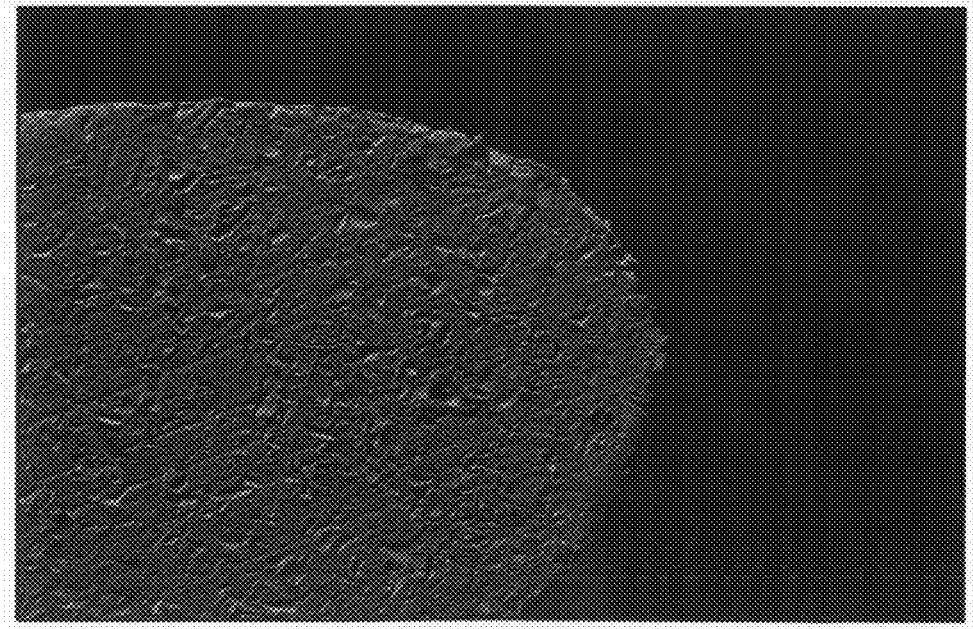
FIG. 19H is an image at 1,000× magnification of the distal tip of a 22 G conventional stylet.
Figure 19I:
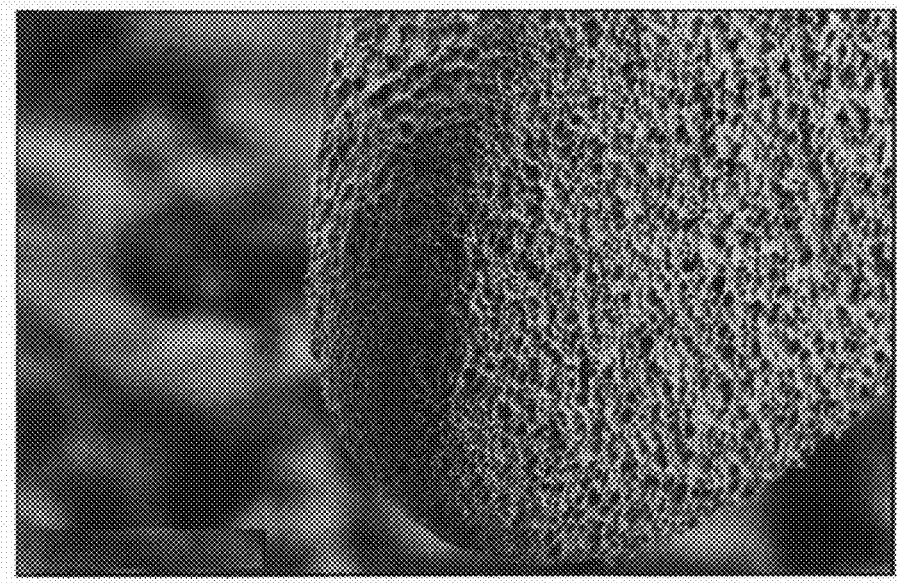
FIG. 19I is an image at 1,000× magnification of the distal tip of a 22 G stylet having a surface modified profile obtained by electrochemical grinding in accordance with an embodiment of the present invention.
Figure 19J:
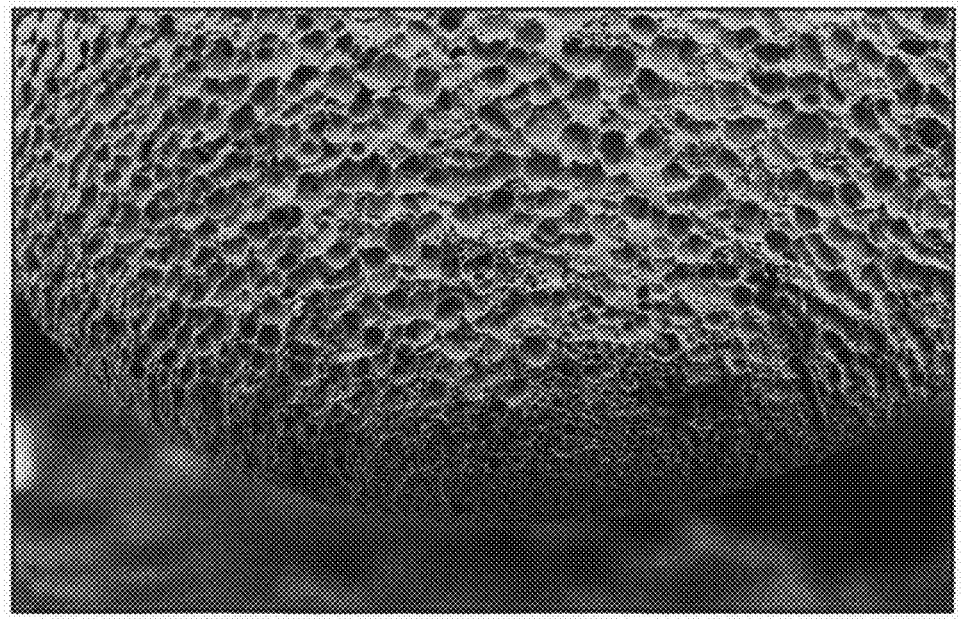
FIG. 19J is an image at 1,000× magnification of the distal tip of a 22 G stylet having a surface modified profile obtained by electrochemical grinding in accordance with an embodiment of the present invention.

FIG. 19E shows the distal tip of a 22 G conventional stylet at 500× magnification. In comparison, FIGS. 19F and 19G show the distal tip of a 22 G stylet having a surface modified profile obtained by electrochemical grinding at 500× magnification. FIG. 19G specifically shows that the surface modified profile is confined to the distal most region of the distal tip. FIG. 19H shows the distal tip of a 22 G conventional stylet at 1,000× magnification. In comparison, FIGS. 19I and 19J show the distal tip of a 22 G stylet having a surface modified profile obtained by electrochemical grinding at 1,000× magnification. As shown in FIGS. 19F, 19G, 19I, and 19J, the distal tip of the 22 G stylet having a surface modified profile has increased micro-texturing as compared to the distal tip of a conventional 22 G stylet shown in FIGS. 19E and 19H.

Figure 19K:
FIG. 19K is an image at 268× magnification of the distal tip of an 18 G stylet having a surface modified profile obtained by sandblasting in accordance with an embodiment of the present invention.
Figure 19L:
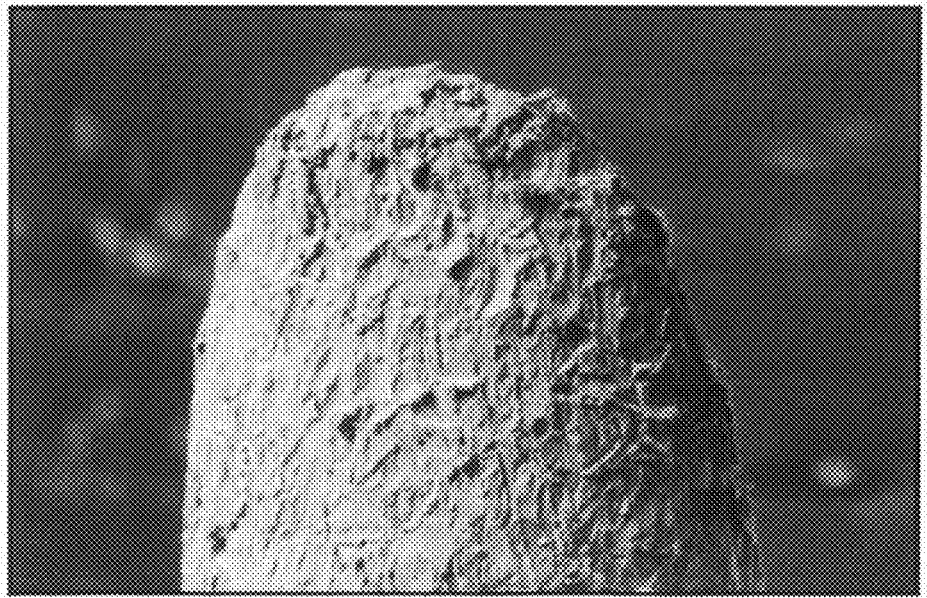
FIG. 19L is an image at 420× magnification of the distal tip of an 18 G stylet having a surface modified profile obtained by sandblasting in accordance with an embodiment of the present invention.

FIG. 19K shows the distal tip of an 18 G stylet having a surface modified profile obtained by sandblasting at 268× magnification. FIG. 19L shows the distal tip of an 18 G stylet having a surface modified profile obtained by sandblasting at 420× magnification. As shown in FIGS. 19K and 19L, the distal tip of the 18 G stylet having a surface modified profile has increased micro-texturing as compared to the distal tip of a conventional 18 G stylet shown in FIG. 19A.

Figure 19M:
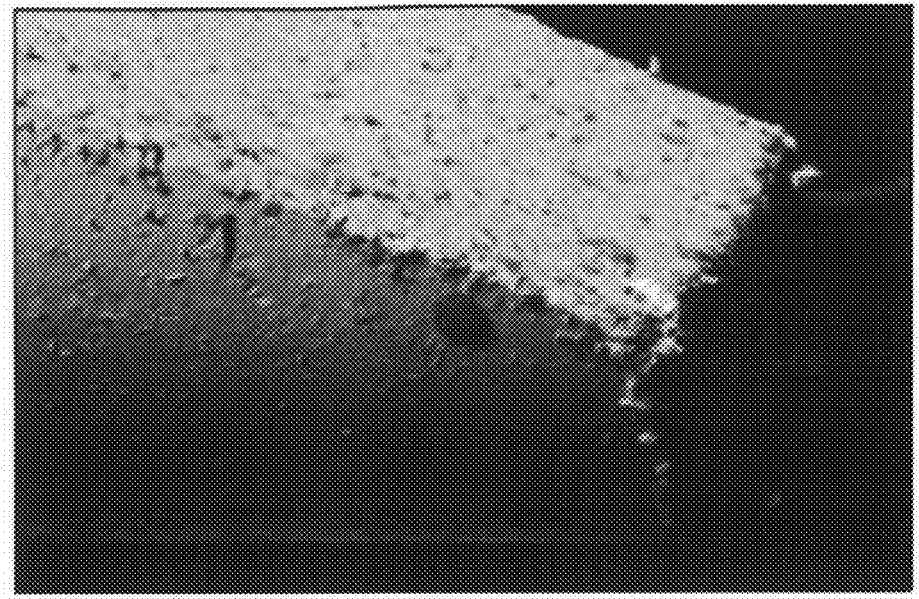
FIG. 19M is an image at 455× magnification of the distal tip of an 18 G stylet having a surface modified profile obtained by blunting and sandblasting in accordance with an embodiment of the present invention.
Figure 19N:
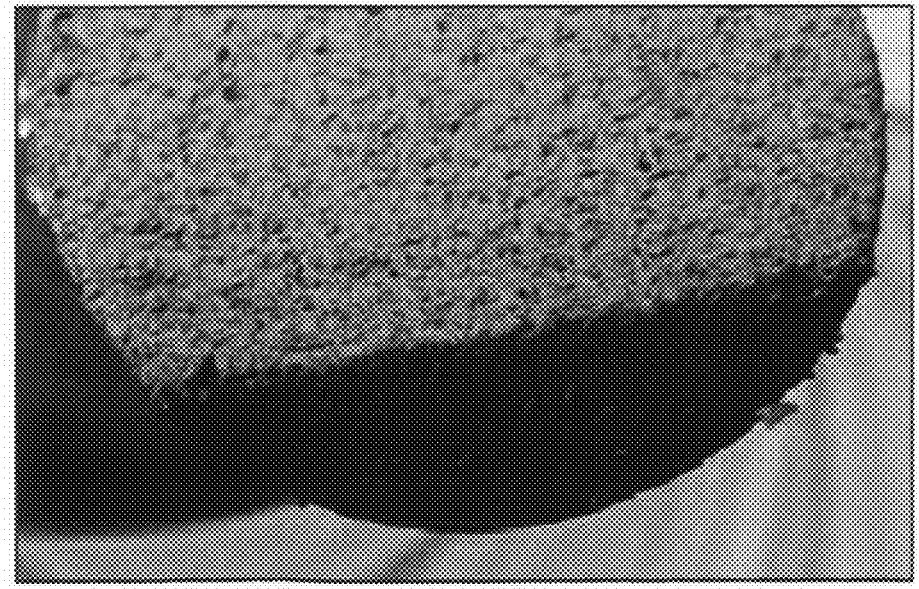
FIG. 19N is an image at 294× magnification of the distal tip of an 18 G stylet having a surface modified profile obtained by blunting and sandblasting in accordance with an embodiment of the present invention.

FIG. 19M shows the distal tip of an 18 G stylet having a surface modified profile obtained by blunting and sandblasting at 455× magnification. FIG. 19N shows the distal tip of an 18 G stylet having a surface modified profile obtained by blunting and sandblasting at 294× magnification. As shown in FIGS. 19M and 19N, the distal tip of the 18 G stylet having a surface modified profile has significantly increased micro-texturing as compared to the distal tip of a conventional 18 G stylet shown in FIG. 19A.

Referring once again to FIGS. 10-11, the surface modified profile 19 may be integrally formed with the distal end 18 of the stylet 15. Optionally, the surface modified profile 19 may be separately formed and subsequently assembled with the distal end 18 of the stylet 15. The surface modified profile 19 may include a beveled edge 19A, which corresponds to a distal bevel 44 of the needle 17, shown in FIG. 11. In one embodiment, at least a portion of the beveled edge 19A having a surface modified profile 19, may extend beyond a portion of the needle 17. The beveled edge 19A of the surface modified profile 19 may form a tip angle B which is greater than the tip angle C of the needle 17. In one embodiment, the tip angle B of the surface modified profile may be from about 20° to about 30°. In a further embodiment, the beveled edge 19A of the surface modified profile 19 may have a bevel length T of from about 0.019 inch to about 0.071 inch.

The stylet 15 having the surface modified profile 19 on the distal end 18 requires a penetration force in excess of typically applied manual pressure to penetrate a skin surface. In one embodiment, prior to performing a medical procedure, the stylet 15 may be nested within the interior 45 of the needle 17 and the distal end 18 of the stylet 15 may extend substantially to the needle tip 20. In one embodiment, the tip angle B of the stylet 15 is selected to maximize the amount of penetration force required to inadvertently penetrate human skin, and minimize the amount of interior space 45 between the distal end 18 of the stylet 15 and the distal bevel 44 of the needle 17 to limit tissue coring during insertion of the distal bevel 44 within a patient.

Figure 20:
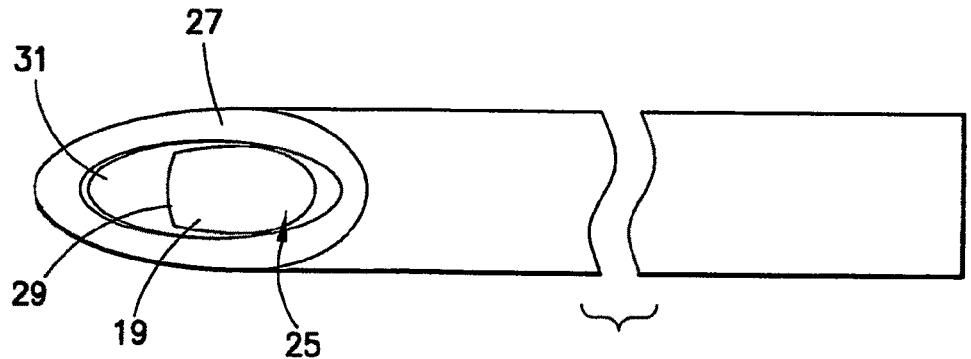
FIG. 20 is a partial top view of a stylet disposed within a needle cannula in accordance with a further embodiment of the present invention.
Figure 21:
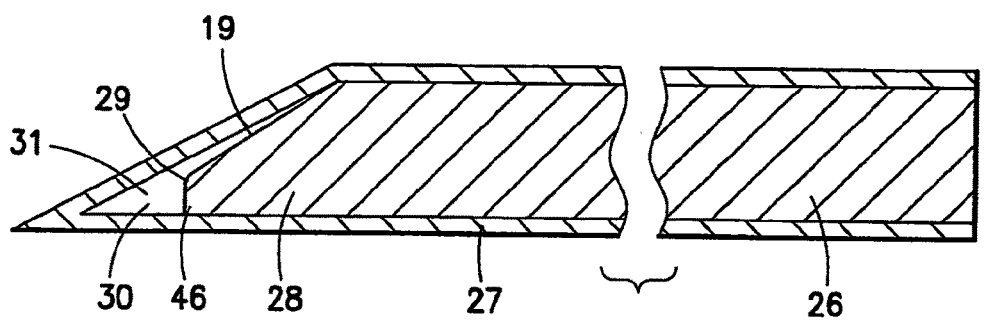
FIG. 21 is a partial cross-sectional side view of the stylet and needle cannula of FIG. 20.

Referring to FIGS. 20-21, another embodiment of the present invention is generally shown. A stylet 25 is provided having an elongated shaft 26 with a distal end 28 having a surface modified profile 19. At least a portion of the distal end 28 is blunted to create a surface modified profile 19 having a blunted tip 29. In one embodiment, the blunted tip 29 has a substantially curved contact surface 46 for further increasing the penetration force required to penetrate a skin surface during accidental or unintentional contact with the distal end 28 of the stylet 25.

Figure 23:
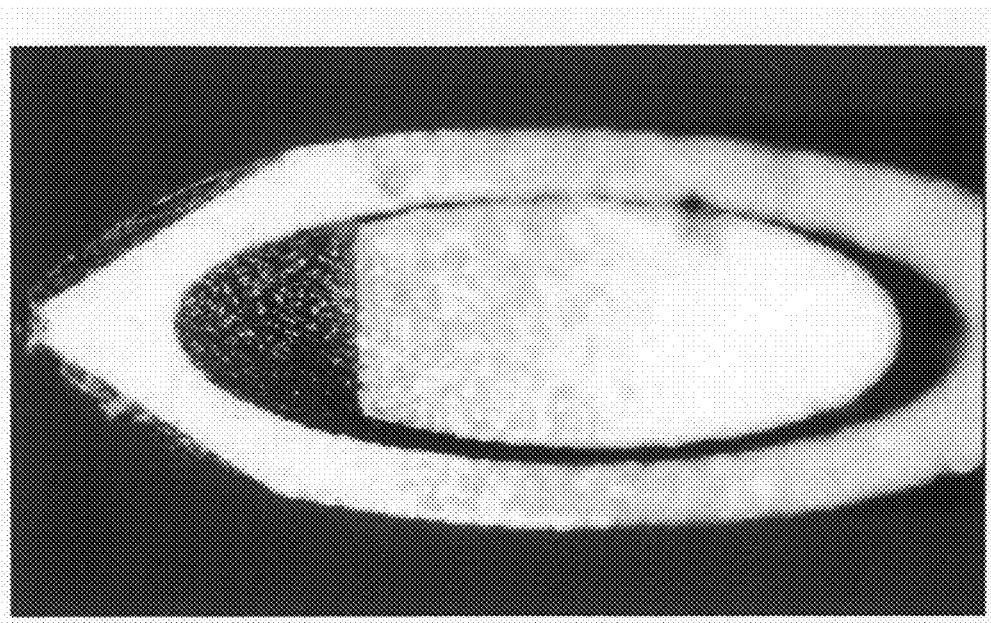
FIG. 23 is an image at 40× magnification of the distal tip of an 18 G stylet having a surface modified profile obtained by blunting the distal end in accordance with an embodiment of the present invention.
Figure 24:
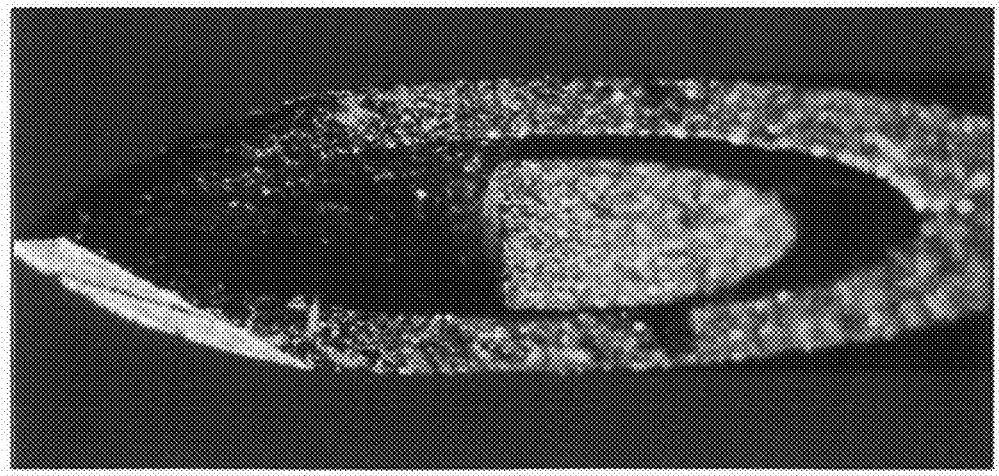
FIG. 24 is an image at 40× magnification of the distal tip of a 22 G stylet having a surface modified profile obtained by blunting the distal end in accordance with an embodiment of the present invention.

FIG. 23 shows an 18 G stylet having a surface modified profile obtained by blunting the distal end of the stylet to remove 0.015 inches of material from the stylet at 40× magnification. FIG. 24 shows a 22 G stylet having a surface modified profile obtained by blunting the distal end of the stylet to remove 0.015 inches of material from the stylet at 40× magnification.

Figure 22:
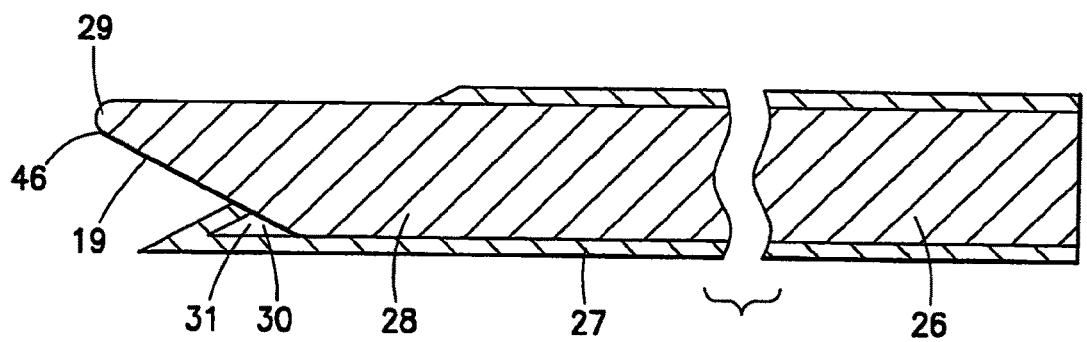
FIG. 22 is a partial cross-sectional side view of the stylet and needle cannula of FIG. 20, showing the stylet in an alternative orientation within the needle.

Referring again to FIGS. 20-21, prior to performing a medical procedure, the stylet 25 may be nested within the interior 31 of the needle 27, and the distal end 28 of the stylet 25 may extend substantially to the needle tip 30. During the medical procedure, the stylet 25 substantially limits the needle 27 from coring tissue by substantially blocking the interior 31 of the needle 27, such as the channel or flow path of the needle 27. As shown in FIG. 21 for example, during the use of the needle 27 in a medical procedure the stylet 25 can be oriented such that the distal end 28 and blunted tip 29 generally correspond to the angle and profile of the needle tip 30. This orientation prevents the blunted tip 29 of the stylet 25 from affecting the performance of the needle 27 during use. After finally withdrawing the needle 27 and stylet 25 from a patient after completing the medical procedure, the stylet 25 can be rotated to extend a portion of the stylet 25 past the needle tip 30, as shown in FIG. 22, to substantially prevent the needle tip 30 from causing needle stick injuries. In this embodiment, the surface modified profile of the stylet 25 is rotated such that it extends past the needle tip 30, thereby increasing the penetration forces required for the combined stylet 25 and needle 30 to penetrate human tissue.

Referring again to FIGS. 1-2, all of the embodiments of the stylet discussed above may also be provided with a stylet handle 13 for user operation. The stylet handle 13 may be adapted to engage the needle hub 3 attached to the proximal end 40A of a needle 10 when the stylet 1, 15, 25, 35 is nested within the cannula of the needle 10, 17, 27. In one embodiment, the stylet includes corresponding orientation portions to tactilely and/or visually provide the orientation between the stylet and the needle. In one embodiment, a stylet in accordance with the present invention as described above, may be provided with a visual and/or tactile indicator disposed within a portion of the elongated shaft. The visual and/or tactile indicator allows a medical practitioner to discern the orientation of the tip portion of the stylet upon insertion or re-insertion of the stylet within the needle.

EXAMPLES

In order to determine the difference in the penetration force of a stylet having a surface modified profile as compared to a conventional stylet, test media samples of 50 A silicone rubber having a thickness of 0.031 inch, a width of 9/16 inch, and a length of approximately 6 inches were prepared and penetrated by both a conventional 18 G stylet and an 18 G stylet having a surface modified profile obtained by electrochemical grinding procedures. Both the 18 G conventional stylet and the 18 G stylet having a surface modified profile were cut to a length of 1¼ inch and mounted with a corresponding size hypodermic needle hub. A penetration speed of 8 ips was used for both the conventional 18 G stylet and the 18 G stylet having a surface modified profile. The 50 A silicone rubber media was provided having little or no tension. To gain a sense of the clinical relevance of the stylet penetration forces in silicone rubber, additional penetration force testing into excised human skin having a thickness of approximately 0.05 inches was performed using the same testing parameters as described with reference to silicone rubber.

Figure 25:
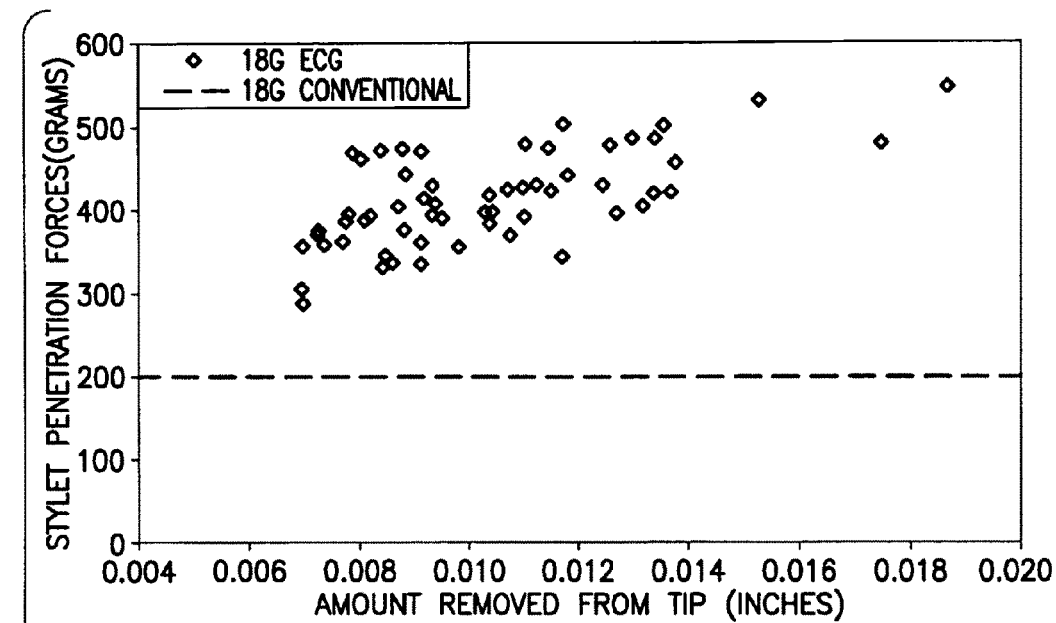
FIG. 25 is a graphical representation of stylet penetration forces vs. the amount of material removed from the distal end of the stylet by electrochemical grinding for an 18 G stylet in silicone rubber.

FIG. 25 is a graphical representation of stylet penetration forces vs. the amount of material removed from the distal end of an 18 G stylet by electrochemical grinding as compared to an 18 G conventional stylet. As shown in FIG. 25, each sample of the 18 G stylet having a surface modified profile exhibited an increased penetration force as compared to the penetration force of a conventional 18 G stylet.

Figure 26:
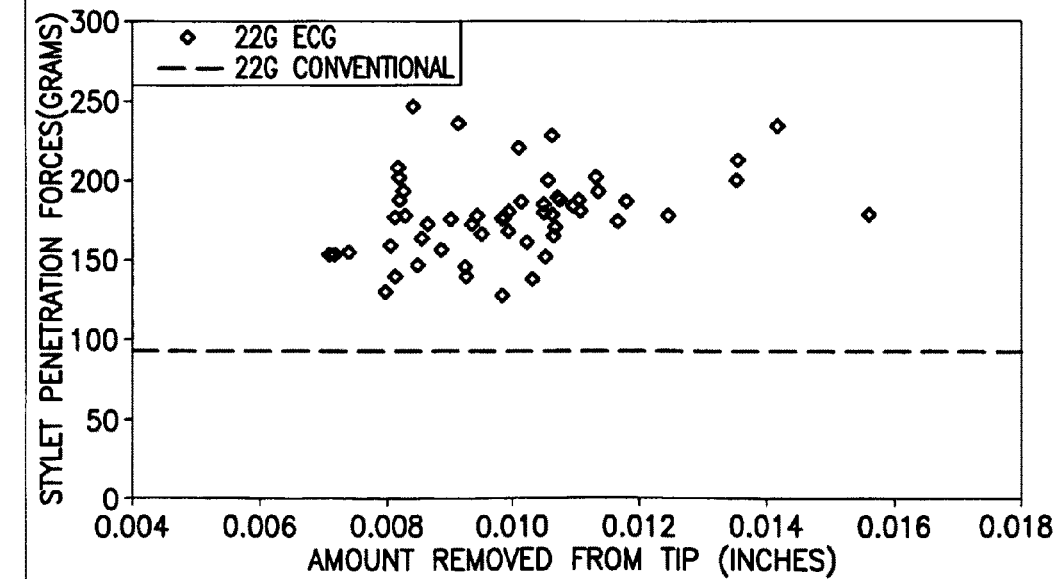
FIG. 26 is a graphical representation of stylet penetration forces vs. the amount of material removed from the distal end of the stylet by electrochemical grinding for a 22 G stylet in silicone rubber.

The same test procedure described above was also performed for a conventional 22 G stylet and a 22 G stylet having a surface modified profile obtained by electrochemical grinding. FIG. 26 is a graphical representation of stylet penetration forces vs. the amount of material removed from the distal end of a 22 G stylet by electrochemical grinding as compared to a 22 G conventional stylet. As shown in FIG. 26, each sample of the 22 G stylet having a surface modified profile exhibited an increased penetration force as compared to the penetration force of a conventional 22 G stylet.

Figure 27:
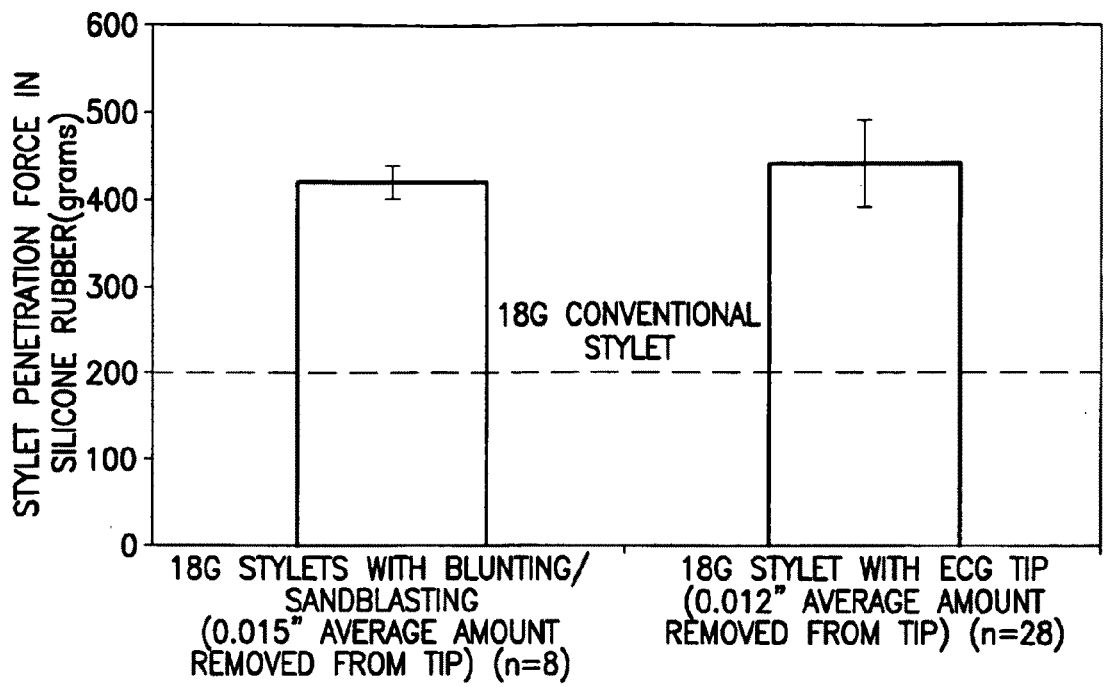
FIG. 27 is a graphical representation of the stylet penetration force in silicone rubber for 18 G stylets having 0.015 inch removed from the distal end by blunting/sandblasting and 0.012 inch removed from the distal end by electrochemical grinding.

FIG. 27 is a graphical representation of the stylet penetration force in silicone rubber for 18 G stylets having an average of 0.015 inch of material removed from the distal end by blunting/sandblasting and an average of 0.012 inch or material removed from the distal end by electrochemical grinding. As shown in FIG. 27, 18 G stylets having a surface modified profile obtained by removing an average of 0.015 inch of material from the distal end by blunting and sandblasting exhibited significantly higher penetration forces than conventional 18 G stylets having an unmodified distal end. Also shown in FIG. 27, 18 G stylets having a surface modified profile obtained by removing an average of 0.012 inch of material from the distal end by electrochemical grinding exhibited significantly higher penetration forces than conventional 18 G stylets having an unmodified distal end.

Figure 28:
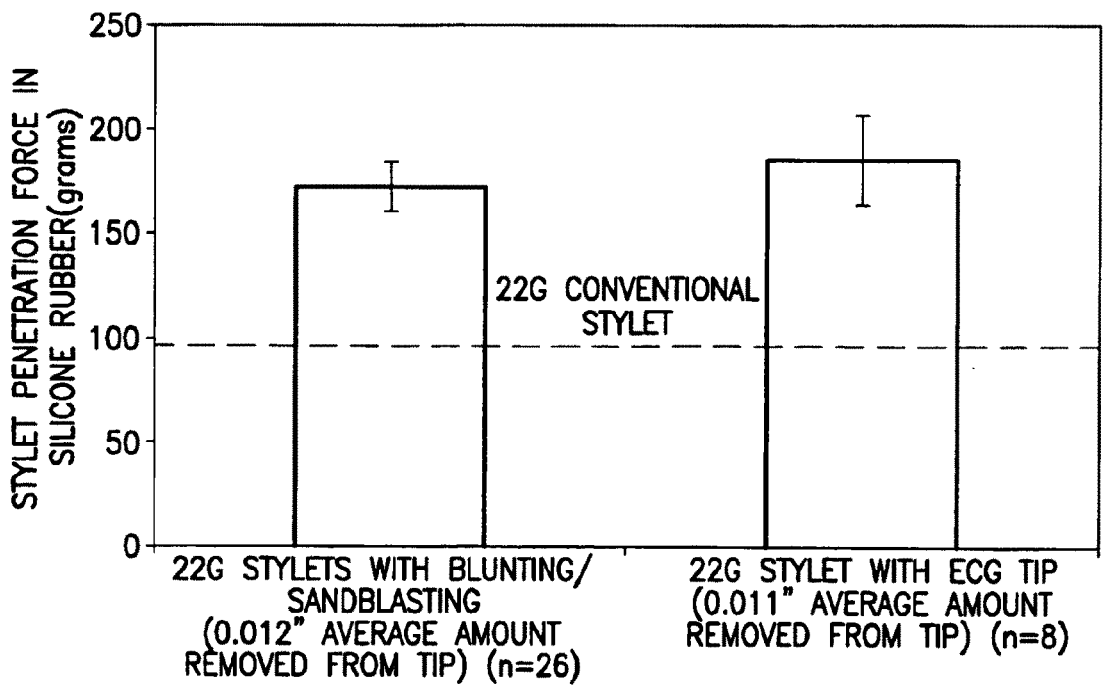
FIG. 28 is a graphical representation of the stylet penetration force in silicone rubber for 22 G stylets having 0.012 inch removed from the distal end by blunting/sandblasting and 0.011 inch removed from the distal end by electrochemical grinding.

FIG. 28 is a graphical representation of the stylet penetration force in silicone rubber for 22 G stylets having an average of 0.012 inch of material removed from the distal end by blunting/sandblasting and an average of 0.011 inch of material removed from the distal end by electrochemical grinding. As shown in FIG. 28, 22 G stylets having a surface modified profile obtained by removing an average of 0.012 inch of material from the distal end by blunting and sandblasting exhibited significantly higher penetration forces than conventional 22 G stylets having an unmodified distal end. Also shown in FIG. 28, 22 G stylets having a surface modified profile obtained by removing an average of 0.011 inch of material from the distal end by electrochemical grinding exhibited significantly higher penetration forces than conventional 22 G stylets having an unmodified distal end.

Figure 29:
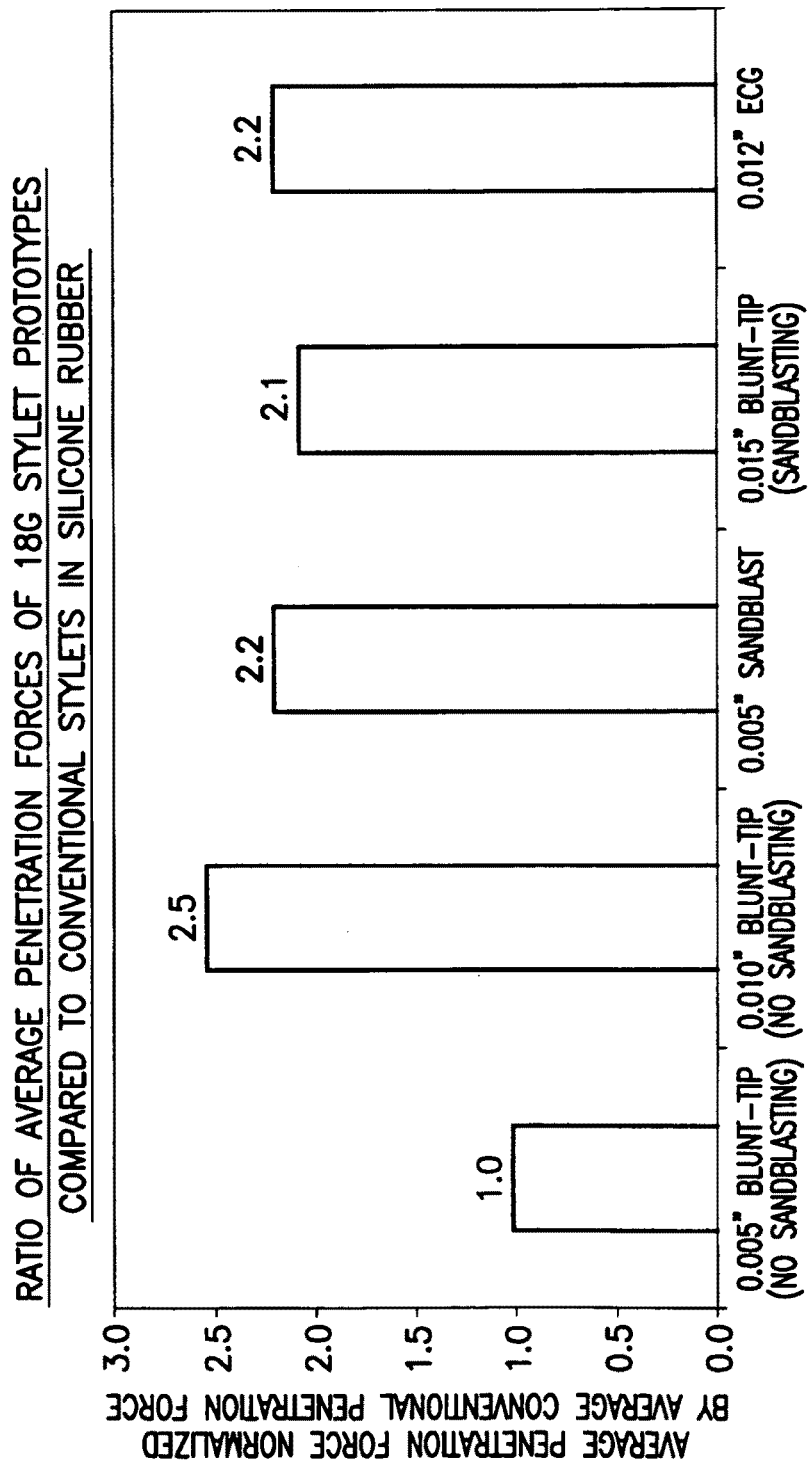
FIG. 29 is a graphical representation of the ratio of average penetration forces for 18 G stylets having a surface modified profile compared to conventional stylets in silicone rubber.

FIG. 29 is a graphical representation of the ratio of average penetration forces normalized by average conventional penetration forces for 18 G stylets. As shown in FIG. 29, each of the 18 G stylets having a surface modified profile obtained by blunting, sandblasting, blunting and sandblasting, or electrochemical grinding exhibited significantly higher penetration forces that conventional 18 G stylets having an unmodified distal end.

Figure 30:
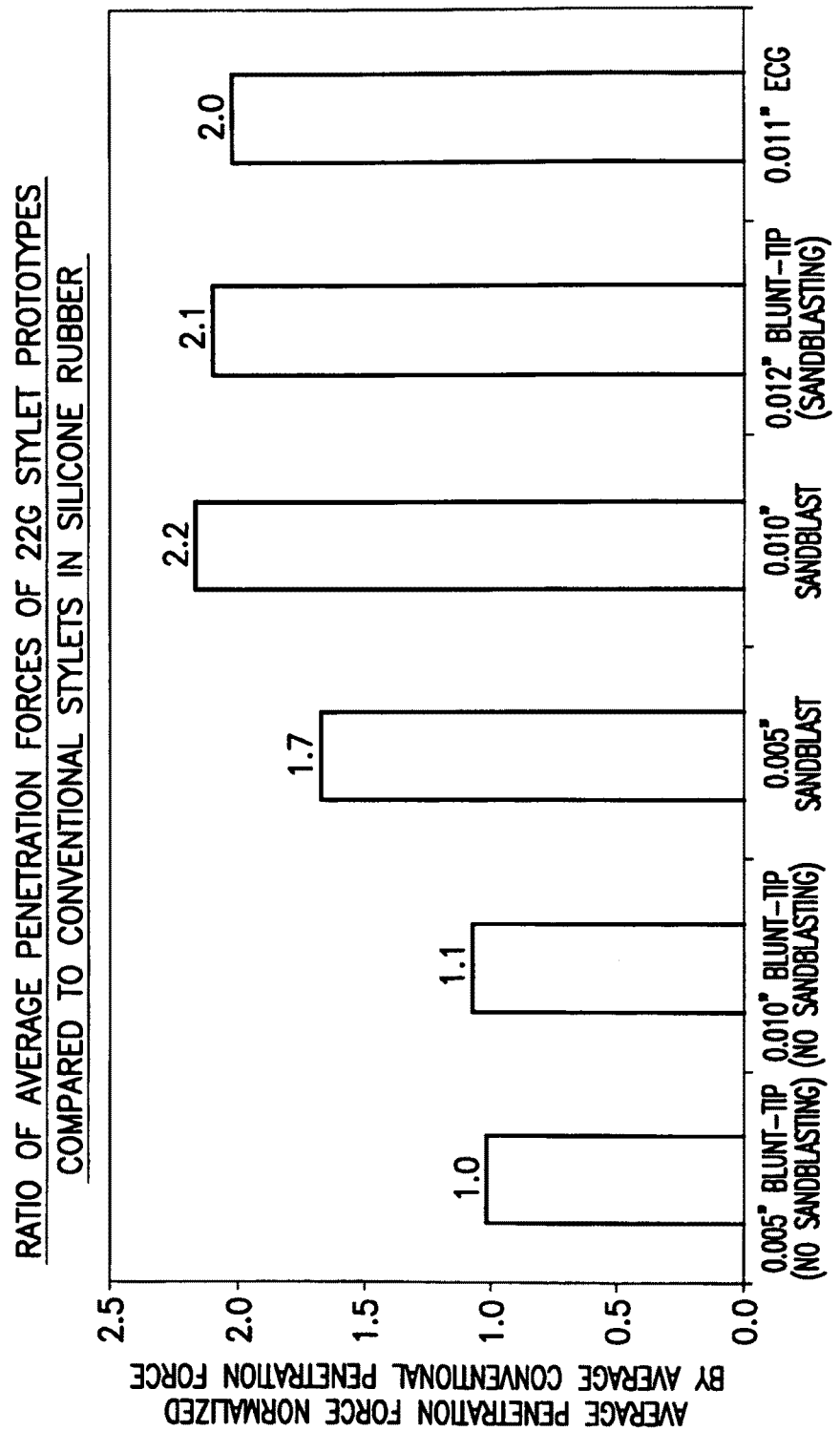
FIG. 30 is a graphical representation of the ratio of average penetration forces for 22 G stylets having a surface modified profile compared to conventional stylets in silicone rubber.

FIG. 30 is a graphical representation of the ratio of average penetration forces normalized by average conventional penetration forces for 22 G stylets. As shown in FIG. 30, each of the 22 G stylets having a surface modified profile obtained by blunting, sandblasting, blunting and sandblasting, or electrochemical grinding exhibited significantly higher penetration forces that conventional 22 G stylets having an unmodified distal end.

Figure 31:
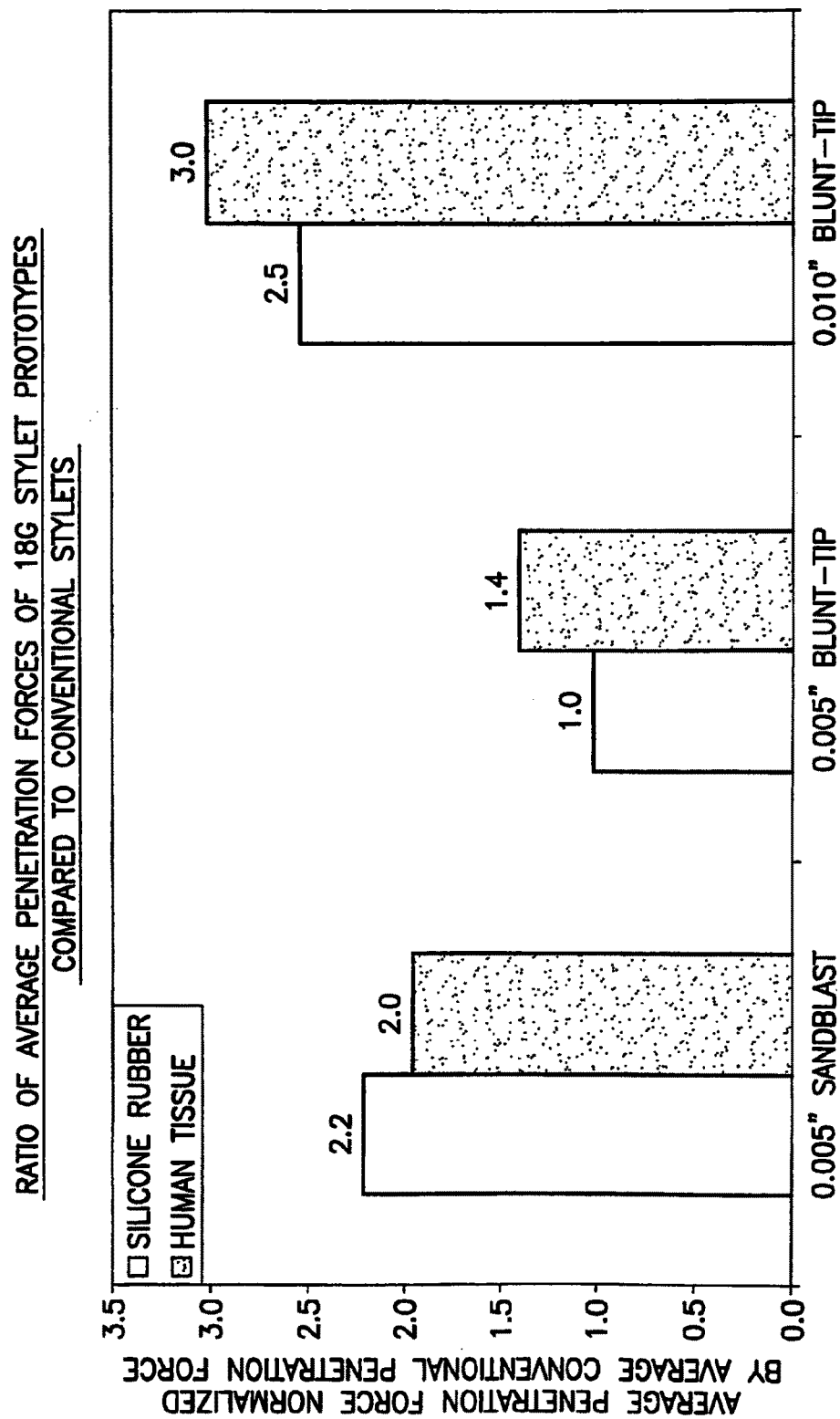
FIG. 31 is a graphical representation of the ratio of average penetration forces for 18 G stylets having a surface modified profile compared to conventional stylets in silicone rubber and human tissue.

FIG. 31 is a graphical representation of the ratio of average penetration forces normalized by conventional penetration forces for 18 G stylets in both silicone rubber and human tissue. As shown in FIG. 31, an 18 G stylet having a surface modified profile obtained by sandblasting procedures to remove 0.005 inch from the distal end of the stylet, an 18 G stylet having a surface modified profile obtained by physically blunting or cutting 0.005 inch from the distal end of the stylet, and an 18 G stylet having a surface modified profile obtained by physically blunting or cutting 0.010 inch from the distal end of the stylet were tested in both silicone rubber and in human tissue. FIG. 31 shows that the 18 G stylet having a surface modified profile obtained by sandblasting has at least twice the penetration force of a conventional 18 G stylet. FIG. 31 also shows that an 18 G stylet having a surface modified profile obtained by blunting to remove 0.005 inch of material has at least 1.4 times the penetration force of a conventional 18 G stylet in human tissue. FIG. 31 also shows that an 18 G stylet having a surface modified profile obtained by blunting to remove 0.010 inch of material has at least 2.5 times the penetration force of a conventional 18 G stylet. As shown in FIG. 31, each of the 18 G stylets having a surface modified profile obtained by sandblasting or blunting exhibited significantly higher penetration forces in human tissue than conventional 18 G stylets having an unmodified distal end.

Figure 32:
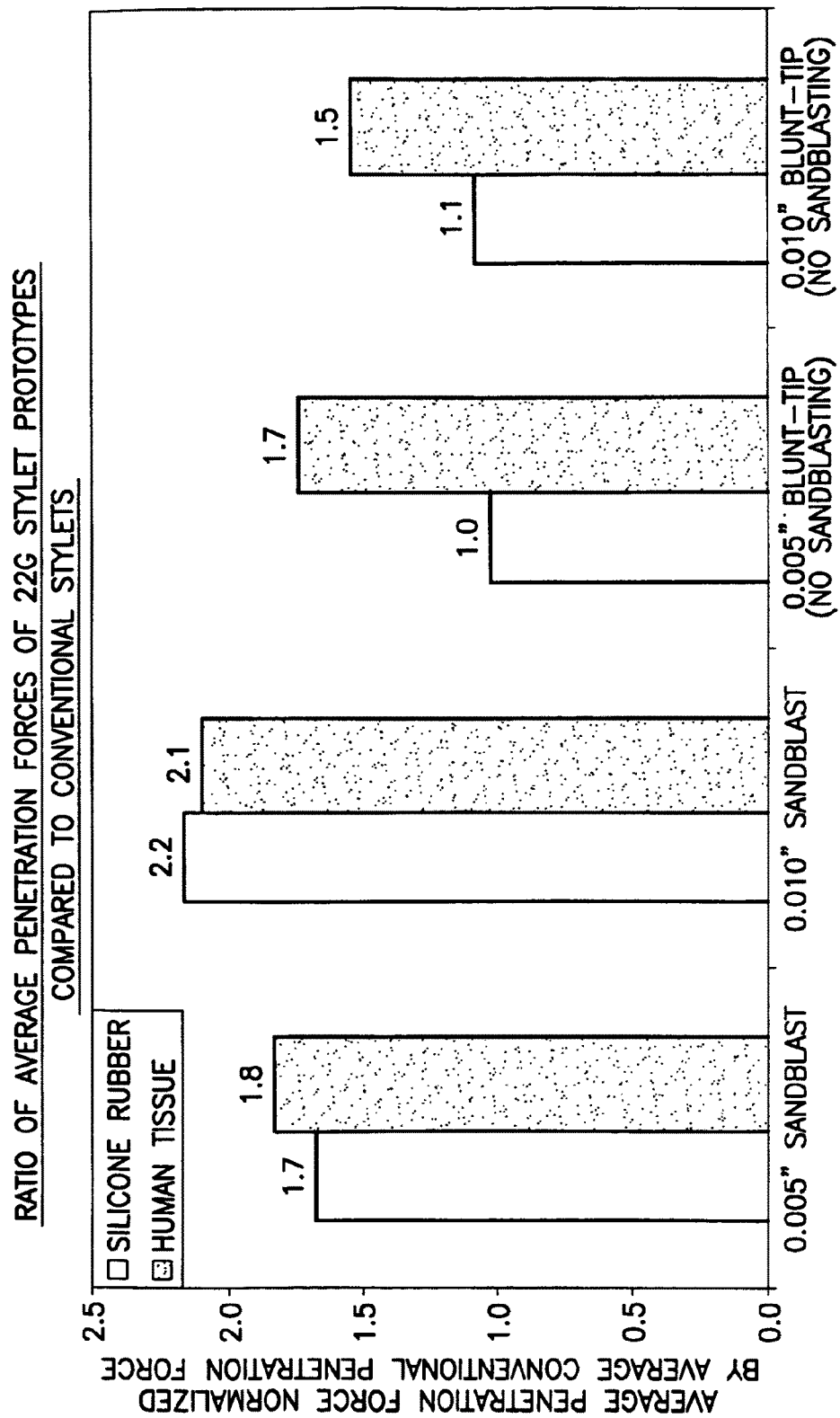
FIG. 32 is a graphical representation of the ratio of average penetration forces for 22 G stylets having a surface modified profile compared to conventional stylets in silicone rubber and human tissue.

FIG. 32 is a graphical representation of the ratio of average penetration forces normalized by conventional penetration forces for 22 G stylets in both silicone rubber and human tissue. As shown in FIG. 32, an 22 G stylet having a surface modified profile obtained by sandblasting procedures to remove 0.005 inch from the distal end of the stylet, a 22 G stylet having a surface modified profile obtained by sandblasting to remove 0.010 inch from the distal end of the stylet, a 22 G stylet having a surface modified profile obtained by physically blunting or cutting 0.005 inch from the distal end of the stylet, and a 22 G stylet having a surface modified profile obtained by physically blunting or cutting 0.010 inch from the distal end of the stylet were tested in both silicone rubber and in human tissue. FIG. 32 shows that the 22 G stylet having a surface modified profile obtained by sandblasting to remove 0.005 inch of material has at least 1.7 times the penetration force of a conventional 22 G stylet. FIG. 32 also shows that the 22 G stylet having a surface modified profile obtained by sandblasting to remove 0.010 inch of material has at least 2.1 times the penetration force of a conventional 22 G stylet. FIG. 32 further shows that a 22 G stylet having a surface modified profile obtained by blunting to remove 0.005 inch of material has at least 1.7 times the penetration force of a conventional 22 G stylet in human tissue. FIG. 32 further shows that a 22 G stylet having a surface modified profile obtained by blunting to remove 0.010 inch of material has at least 1.5 times the penetration force of a conventional 22 G stylet in human tissue.

While several embodiments of the invention were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A safety stylet for insertion within a cannula of a needle, comprising a solid elongated stylet shaft having a proximal end adapted for engagement with a needle hub, and a distal end comprising a dull planar contact surface, wherein the contact surface has a surface modified profile, wherein the surface modified profile comprises a roughened surface.

2. The stylet of claim 1, wherein the surface modified profile further comprises a blunted region.

3. The stylet of claim 1, wherein the surface modified profile has been obtained through at least one of a sandblasting process, an electrochemical grinding process, a mechanical grinding process, and an etching process.

4. The stylet of claim 1, wherein at least 0.002 inch of material has been removed from the distal end to form the surface modified profile.

5. The stylet of claim 1, wherein the surface modified profile further comprises a beveled edge.

6. The stylet of claim 5, wherein the beveled edge has a tip angle of from about 20° to about 30°.

7. The stylet of claim 1, wherein the solid elongated shaft is formed of a polymeric material.

8. The stylet of claim 1, wherein the solid elongated shaft is formed of a metal or metal alloy, the distal end having an increased bevel angle compared to a bevel angle of the needle cannula for increasing the penetration force.

9. A safety stylet for insertion within a cannula of a needle, comprising a solid elongated stylet shaft having a proximal end adapted for engagement with a needle hub, and a distal end comprising a dull contact surface, wherein the contact surface has a surface modified profile, wherein the surface modified profile comprises a blunted surface.

10. The stylet of claim 9, wherein the surface modified profile has been obtained through at least one of a sandblasting process, an electrochemical grinding process, a mechanical grinding process, a buffing process, and an etching process.

11. The stylet of claim 9, wherein at least 0.002 inch of material has been removed from the distal end to form the surface modified profile.

12. The stylet of claim 9, wherein the distal end further comprises a beveled edge.

13. The stylet of claim 12, wherein the beveled edge has a tip angle of from about 20° to about 30°.

14. The stylet of claim 9, wherein the solid elongated shaft is formed of a polymeric material.

15. The stylet of claim 9, wherein the solid elongated shaft is formed of a metal or metal alloy, the distal end having an increased bevel angle compared to a bevel angle of the needle cannula for increasing the penetration force.

* * * * *